US011992416B2

United States Patent
Ek

(10) Patent No.: US 11,992,416 B2
(45) Date of Patent: *May 28, 2024

(54) MULTICOMPONENT ARTICULAR SURFACE IMPLANT

(71) Applicant: ARTHROSURFACE INCORPORATED, Franklin, MA (US)

(72) Inventor: Steven W. Ek, Bolton, MA (US)

(73) Assignee: ARTHROSURFACE INCORPORATED, Franklin, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/516,467

(22) Filed: Nov. 1, 2021

(65) Prior Publication Data

US 2022/0296383 A1 Sep. 22, 2022

Related U.S. Application Data

(63) Continuation of application No. 16/054,224, filed on Aug. 3, 2018, now Pat. No. 11,160,663.

(Continued)

(51) Int. Cl.
*A61F 2/42* (2006.01)
*A61B 17/17* (2006.01)
(Continued)

(52) U.S. Cl.
CPC ........ *A61F 2/4202* (2013.01); *A61B 17/1775* (2016.11); *A61F 2/30756* (2013.01); *A61F 2002/30332* (2013.01); *A61F 2002/30387* (2013.01); *A61F 2002/30507* (2013.01); *A61F 2002/30604* (2013.01);
(Continued)

(58) Field of Classification Search
CPC ............ A61F 2/4202; A61F 2002/4207; A61F 2002/4205; A61F 2/3868; A61F 2/4618; A61F 2/30756; A61F 2002/30604; A61F 2002/30383; A61F 2002/30387; A61F 2002/30751; A61F 2220/0025

See application file for complete search history.

(56) References Cited

U.S. PATENT DOCUMENTS 6,228,119 B1 * 5/2001 Ondrla .................. A61F 2/4081
623/19.11
2002/0147498 A1 * 10/2002 Tallarida ................ A61B 90/06
623/20.14
(Continued)

*Primary Examiner* — Javier G Blanco
(74) *Attorney, Agent, or Firm* — GOODWIN PROCTER LLP

(57) ABSTRACT

A multicomponent implant system includes a multicomponent implant comprising a base plate and a load plate. The base plate includes a bone facing surface and a base plate interface surface. The load plate includes a load plate interface surface and a load bearing surface, the load bearing surface being substantially parallel to the load plate interface surface and having a contour substantially corresponding to a contour of a removed portion of the articular surface. Both the load plate interface surface and base plate interface surface have a contour substantially corresponding to the contour of the load bearing surface. The load plate is configured to be advanced in an arcuate direction to slidably couple the load plate to the base plate after the base plate has been secured within the first excision site by an anchor.

17 Claims, 23 Drawing Sheets

Related U.S. Application Data

(60) Provisional application No. 62/541,359, filed on Aug. 4, 2017.

(51) Int. Cl.
  *A61F 2/30* (2006.01)
  *A61F 2/38* (2006.01)
  *A61F 2/46* (2006.01)

(52) U.S. Cl.
  CPC ............. *A61F 2002/30751* (2013.01); *A61F 2002/30761* (2013.01); *A61F 2002/3085* (2013.01); *A61F 2/3868* (2013.01); *A61F 2002/4205* (2013.01); *A61F 2002/4207* (2013.01); *A61F 2/4618* (2013.01)

(56) References Cited

U.S. PATENT DOCUMENTS

| | | | | |
|---|---|---|---|---|
| 2011/0213375 | A1* | 9/2011 | Sikora | A61B 17/1764 606/87 |
| 2014/0018931 | A1* | 1/2014 | Gillard | A61F 2/4202 623/18.11 |
| 2014/0128985 | A1* | 5/2014 | Sanders | A61F 2/4225 623/21.18 |
| 2014/0296995 | A1* | 10/2014 | Reiley | A61F 2/4202 623/21.18 |

* cited by examiner

MULTICOMPONENT ARTICULAR SURFACE IMPLANT

CROSS REFERENCE TO RELATED APPLICATIONS

This application is a Continuation Application of U.S. application Ser. No. 16/054,224, filed Aug. 3, 2018, which claims the benefit of U.S. Provisional Application Ser. No. 62/541,359, filed Aug. 4, 2017, the entire disclosures of which are fully incorporated herein by reference.

FIELD

The present disclosure is related to devices and methods for the repair of defects that occur in articular cartilage on the surface of bones, and particularly the ankle.

BACKGROUND

Articular cartilage, found at the ends of articulating bones in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspect of native hyaline cartilage and tends to be less durable.

In some cases, it may be necessary or desirable to repair the damaged articular cartilage using one or more implants. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

By way of an overview, one embodiment of the present disclosure features systems and methods for repairing all or a portion of a first and a second articular surface associated with a first and a second bone, respectively, of a joint. The joint may include any joint such as, but not limited to, a talocrural joint, an ankle joint, a knee joint, a shoulder joint, toe joint, finger joint, or the like. As described herein, the systems and methods include a first or cooperating implant system to be secured to the first bone of the joint, and a multicomponent implant system to be secured to the second bone of the joint. The multicomponent implant system includes one or more multicomponent implant anchors, one or more base plates configured to be secured to the multicomponent implant anchors, and one or more load plates configured to be slidably received and coupled to the base plate. The base plate and the load plate define a multicomponent implant.

The load plate includes a load bearing surface having a contour based on and/or substantially corresponding to the contour of the patient's removed articular surface of the second bone, and a load plate interface surface that has a contour substantially corresponding to the contour of the load bearing surface. The base plate has a bone facing surface which engages with multicomponent implant anchor secured in the second bone within an excision site formed in the second bone, and a base plate interface surface. The base plate interface surface has a contour (at least in a distal to proximal direction) that also substantially corresponds to the contour of the load plate interface surface (at least in the distal to proximal direction). The load plate interface surface is configured to be advanced into a space between the base plate interface surface and the cooperating implant system installed in the first bone of the joint, generally along an arcuate direction having a curvature substantially corresponds to the contour of the load plate interface surface (at least in the distal to proximal direction). The load plate interface surface and the base plate interface surface may form a tongue and groove style connection wherein the tongue and groove may have any interlocking shape. The base plate may have a maximum thickness T1 in a distal region that is less than the height H2 of an intermediate region of the space formed between the base plate and the installed cooperating implant system. Because the maximum thickness T1 in the distal region is less than the height H2 of the intermediate region, the base plate may be slid/advanced into the space initially and secured to the multi-component implant anchor within the excision site formed in the second bone without having to separate the first and second bones of the joint. This helps to reduce the overall trauma incurred in performing the procedure.

Figure 1:
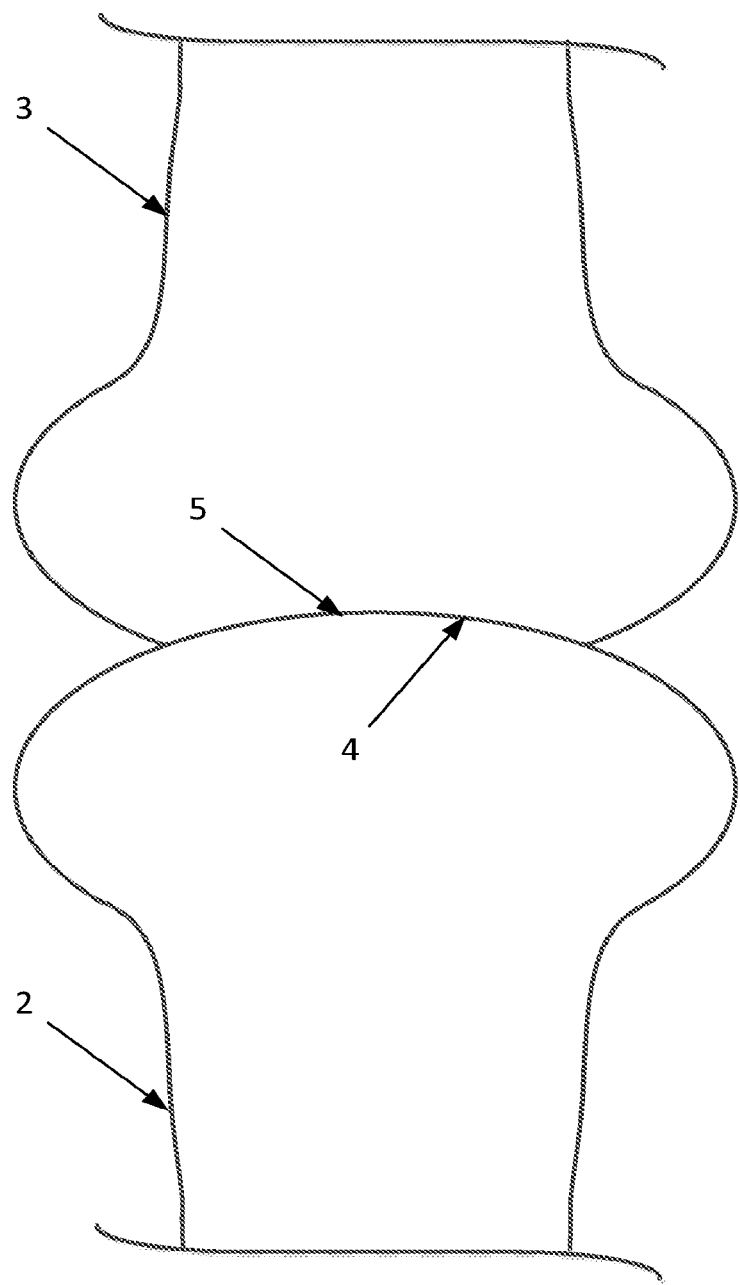
FIG. 1 illustrates a front view of a joint formed by a first and a second bone which the first and second implant systems may be used to repair.

Turning to FIG. 1, a front view of an exemplary joint 1 is generally illustrated. The joint 1 includes a first and a second bone 2, 3 having a first and a second cooperating articular surface 4, 5, respectively. As discussed herein, one or more generally cylindrical cuts will be generally simultaneously made into first and second articular surfaces 4,5 of the bones 2, 3 to form a first and a second implant site into which a first and a second implant system will be secured.

Figure 2:
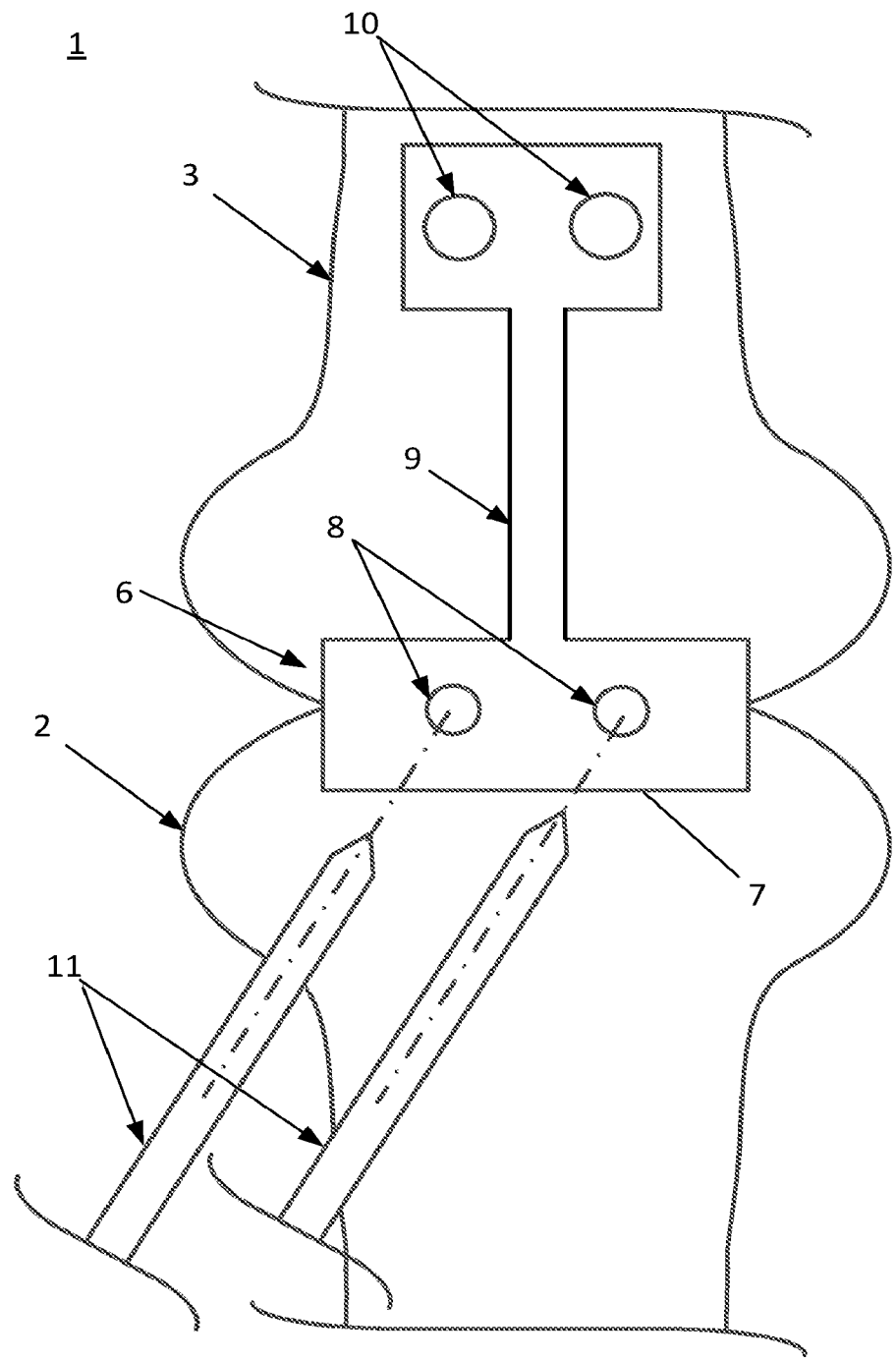
FIG. 2 illustrates a front view of one embodiment of a guide for establishing the excision sites in the first and second bones of FIG. 1.
Figure 3:
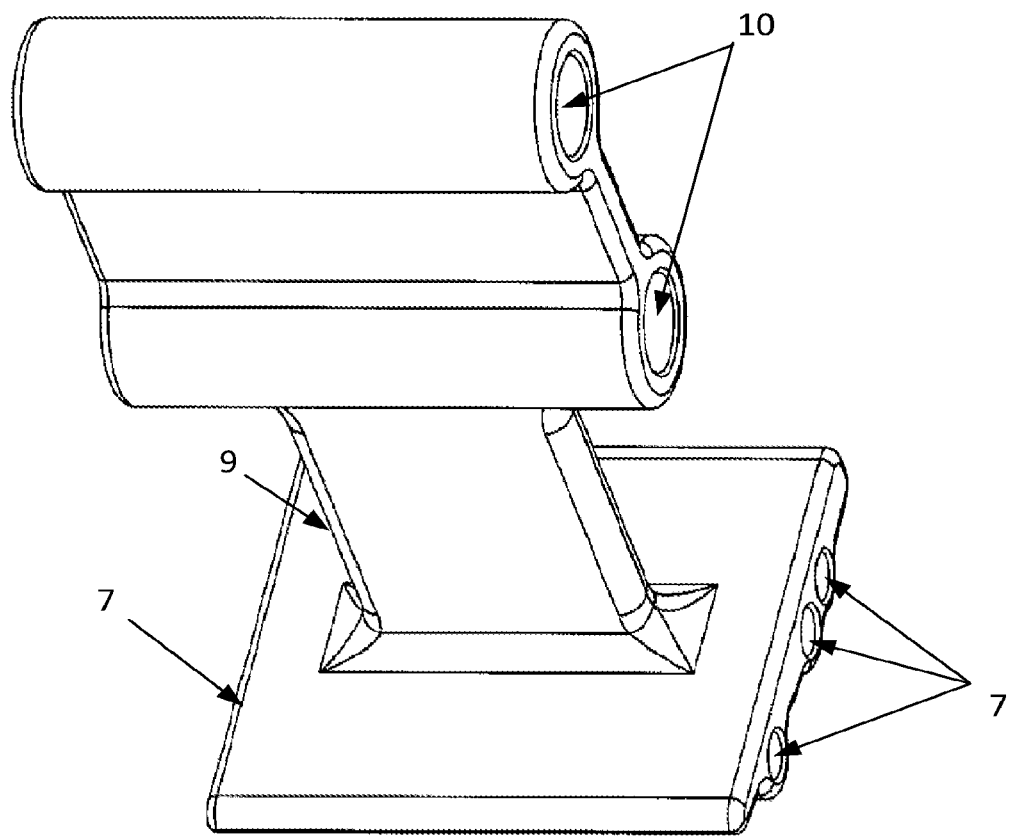
FIG. 3 illustrates a perspective view of one embodiment of a guide consistent with the present disclosure.

A guide may be used to form the first and second implant site in the first and/or second bone 2, 3. With reference to FIGS. 2 and 3, the guide 6 may include a guide body 7 defining one or more (e.g., but not limited to, two or more) alignment passageways 8 having an opening and an exit at opposite ends thereof. The guide 6 may be aligned (e.g., but not limited to, visually aligned) with the articular surfaces 4, 5 of the first and second bones 2, 3 such that the alignment passageways 8 are generally aligned perpendicular to the first and second bones 2, 3 (e.g., but not limited to, facing generally front to rear) and generally aligned with the defects in the articular surfaces 4, 5. The guide 6 may include a handle 9 for the user to grasp and manipulate the guide 6, and also optionally one or more stabilizing passageways 10 through which one or more screws, pins, or the like (not shown for clarity) may secure the guide 6 to one or more of the bones 2, 3 such that the position/alignment of the alignment passageways 8 is generally fixed relative to the bones 2, 3 and/or the articular surfaces 4, 5 until the guide 6 is removed.

Once the guide 6 is aligned, one or more alignment/guide pins 11 may be advanced at least partially through the alignment passageways 8 and secured into one or more of the bones 2, 3 and/or articular surfaces 4, 5. In the embodiment illustrated in FIG. 2, the guide 6 includes two alignment passageways 8 through which two alignment/guide pins 11 are advanced, though it should be understood that the guide 6 may include only a single alignment passageway 8 for use with a single alignment/guide pin 11, or more than two alignment passageways 8 for use with more than two alignment/guide pins 11.

Figure 4:
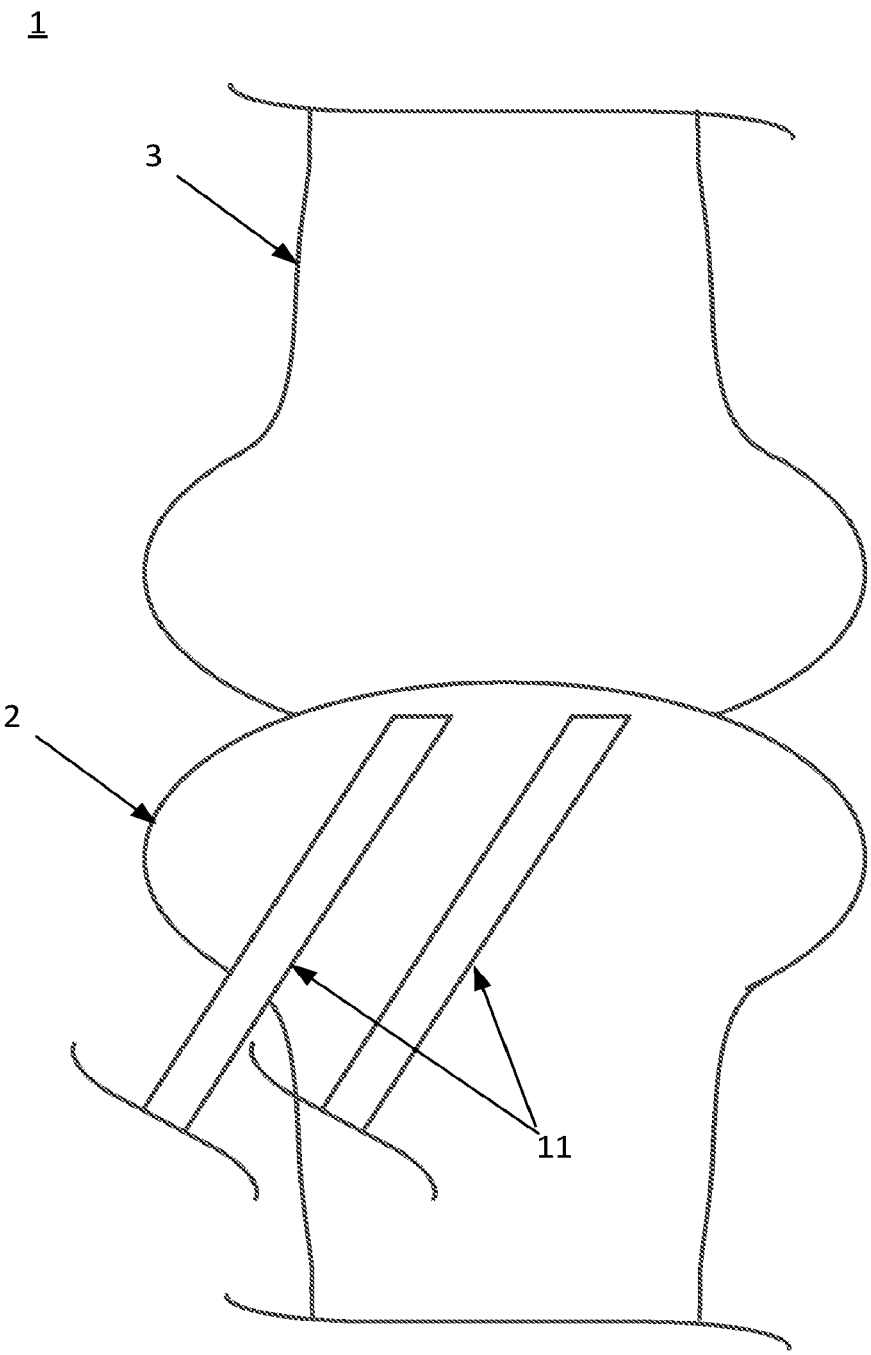
FIG. 4 illustrates a front view of one embodiment of guide pins installed in the joint of FIG. 1.

Once the desired alignment/guide pins 11 are secured, the guide 6 may be removed from the joint 1 leaving behind the secured alignment/guide pins 11, as generally illustrated in FIG. 4. Next, one or more cannulated drill bits (e.g., but not limited to, core drilling bits) may be advanced over the alignment/guide pins 11 to form an excision site in the bones 2, 3. As may be appreciated, the cannulated drilling bit forms a generally cylindrical pathway as it is advanced over the alignment/guide pin 11 and into the first and second bones 2, 3. As used herein, the resulting excision sites formed as the drilling bit is advanced into the bones 2, 3 is collectively referred to as a generally cylindrical excision site. The generally cylindrical excision site therefore has a diameter that is approximately equal to the diameter of the drilling bit.

Figure 5:
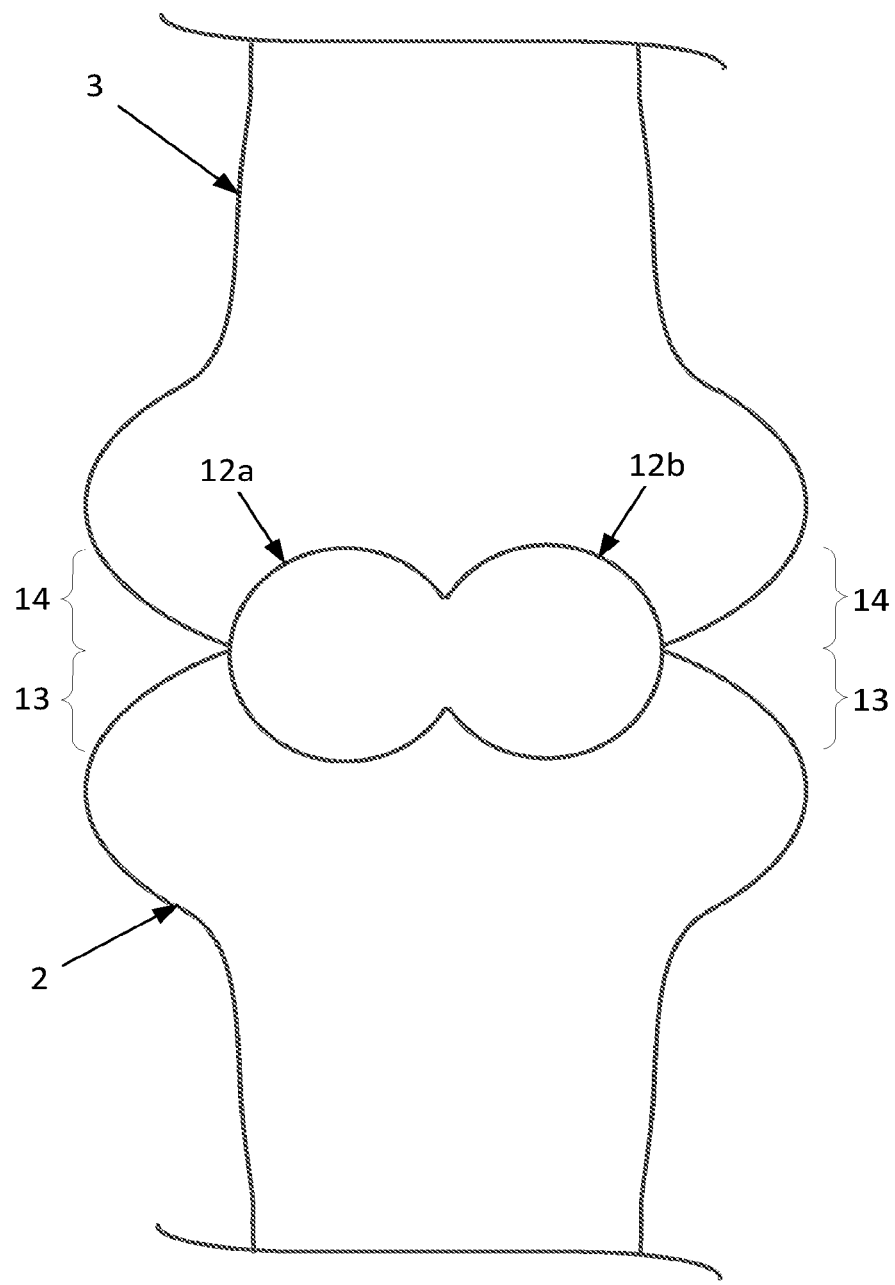
FIG. 5 illustrates a front view of excision sites formed in the first and second bones of FIG. 1.

According to one embodiment, the guide 6 may include two alignment passageways 8 that are spaced apart from each other (e.g., but not limited to, spaced apart from each other along an axis that is generally transverse to length of the bones 2, 3). The spacing of the alignment passageways 8 is selected such that the generally cylindrical pathways of two adjacent drilling bits partially overlap to form two or more overlapping generally cylindrical excision sections 12a, 12b, as generally illustrated in FIG. 5 formed in the first and second bones 2, 3. The overlapping generally cylindrical excision sections 12a, 12b formed in the first and second bones 2, 3 each define part of a first and a second implant site 13, 14 formed in the first and second bones 2, 3, respectively. As can be seen, the first and second implant sites 13, 14 include a truncated portion of the overlapping generally cylindrical excision sections 12a, 12b. Put another way, the first implant site 13 includes a lower truncated portion of the overlapping generally cylindrical excision sections 12a, 12b while the second implant site 14 includes an upper truncated portion of the overlapping generally cylindrical excision sections 12a, 12b.

Figure 6:
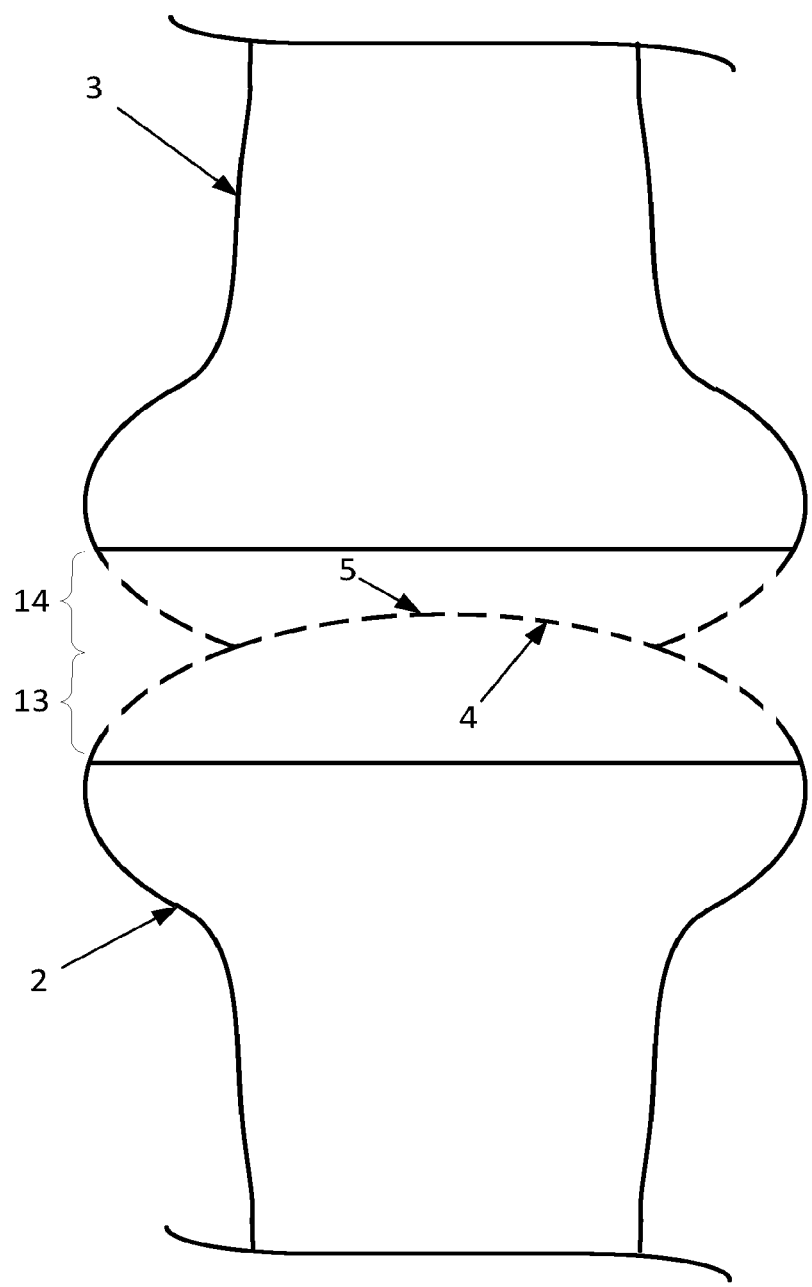
FIG. 6 illustrates a side view of excision sites formed in the first and second bones of FIG. 1.

Turning now to FIG. 6, a side view of the first and second implant sites 13, 14 including the removed original articular surfaces 4, 5 shown in dotted lines for reference. As explained herein, a first and second cooperating implant will be secure within/to the first and second implant sites 13, 14 to replace the removed original articular surfaces 4, 5. According to one embodiment, a multicomponent implant system may be secured to the second bone 3 after a cooperating implant system is secured to first bone 2.

Installation of the cooperating implant system into the first implant sites 13 will be described first. Prior to removing the patient's articular surface 4, 5, the contours of the patient's original articular surface may be determined based on one or more measures directly taken of the patient's original articular surface 4, 5 (e.g., as generally described in one or more of U.S. Pat. Nos. 7,678,151 and 8,177,841, which are fully incorporated herein by reference) and/or indirectly taken (e.g., using Computed Tomography (CT) scanning imaging techniques, Magnetic Resonance Imaging (MRI) techniques, Positron Emission Tomography (PET) techniques, PET-CT techniques, x-ray imaging techniques, or the like. As explained further herein, the cooperating implant system may include an implant having a load bearing surface with a contour that is based on and/or substantially corresponds to the contour of the patient's removed articular surface, and one or more anchors that are configured to be coupled to the implant and to secure the implant to the bone within the excision site.

Figure 7:
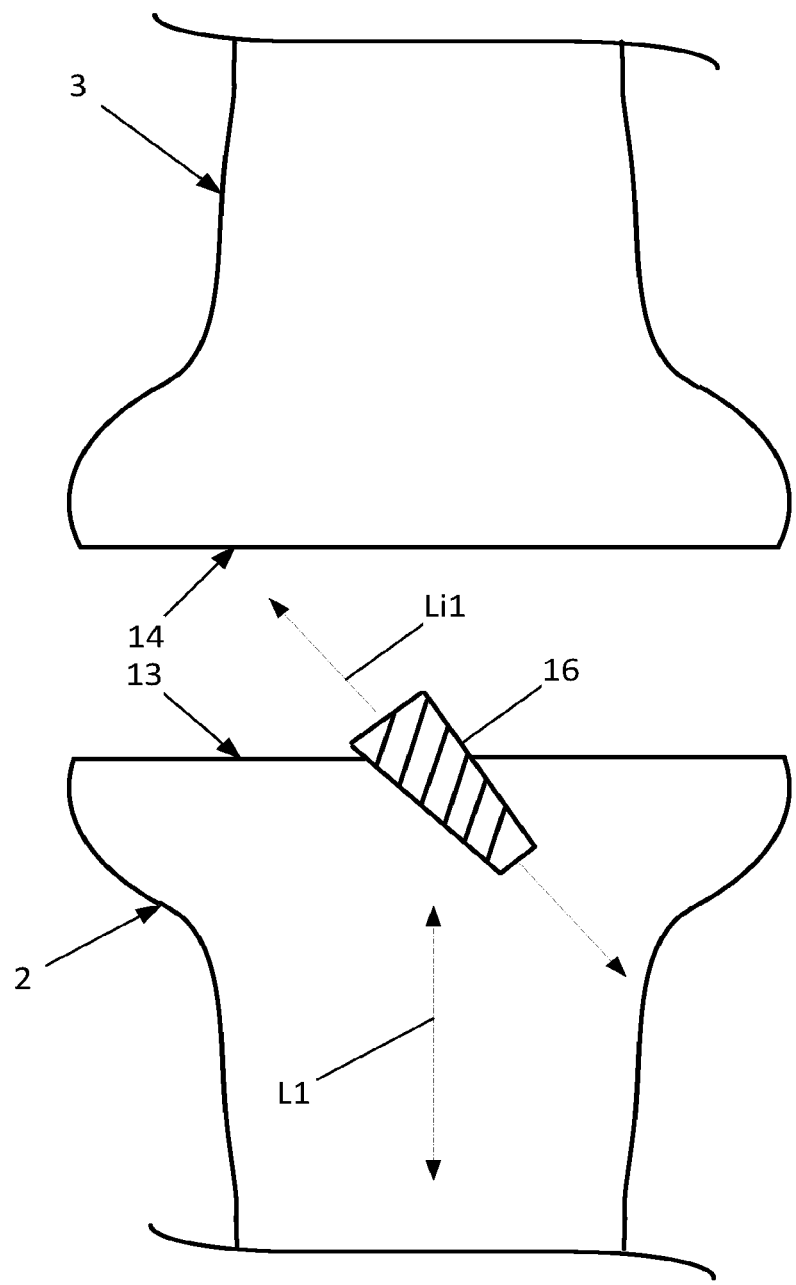
FIG. 7 illustrates a side view of an anchor installed in the first bone.

Turning to FIG. 7, one or more cooperating implant anchors 16 of the cooperating implant system are shown secured to the first bone 2 within the first implant site 13. The position of the cooperating implant anchor(s) 16 with respect to the first implant site 13 may be determined using one or more guides or the like. The cooperating implant anchor 16 may include one or more threaded portions, barbed portions, ribs, protrusions, or the like (which may, for example, extend circumferentially fully or partially around all or a portion of the shank of the anchor 16) configured to engage and retain the cooperating implant anchor 16 to the first bone 2 within one or more of the overlapping generally cylindrical excision sections 12a, 12b (not visible in FIG. 7). The cooperating implant anchor 16 may include a longitudinal axis Li1 that may be disposed generally parallel to the longitudinal axis L1 of the first bone 2; however, it should be understood that longitudinal axis Li1 may be disposed at any angle between 0 and 90 degrees (such as, but not limited to, between 30 and 80 degrees, between 40 and 60 degrees, or the like). It should also be understood that when the cooperating implant system includes multiple cooperating implant anchors 16, the longitudinal axes Lit two or more of the cooperating implant anchors 16 may be disposed at the same and/or different angles with respect to the longitudinal axis L1 of the first bone 2.

Figure 8A:
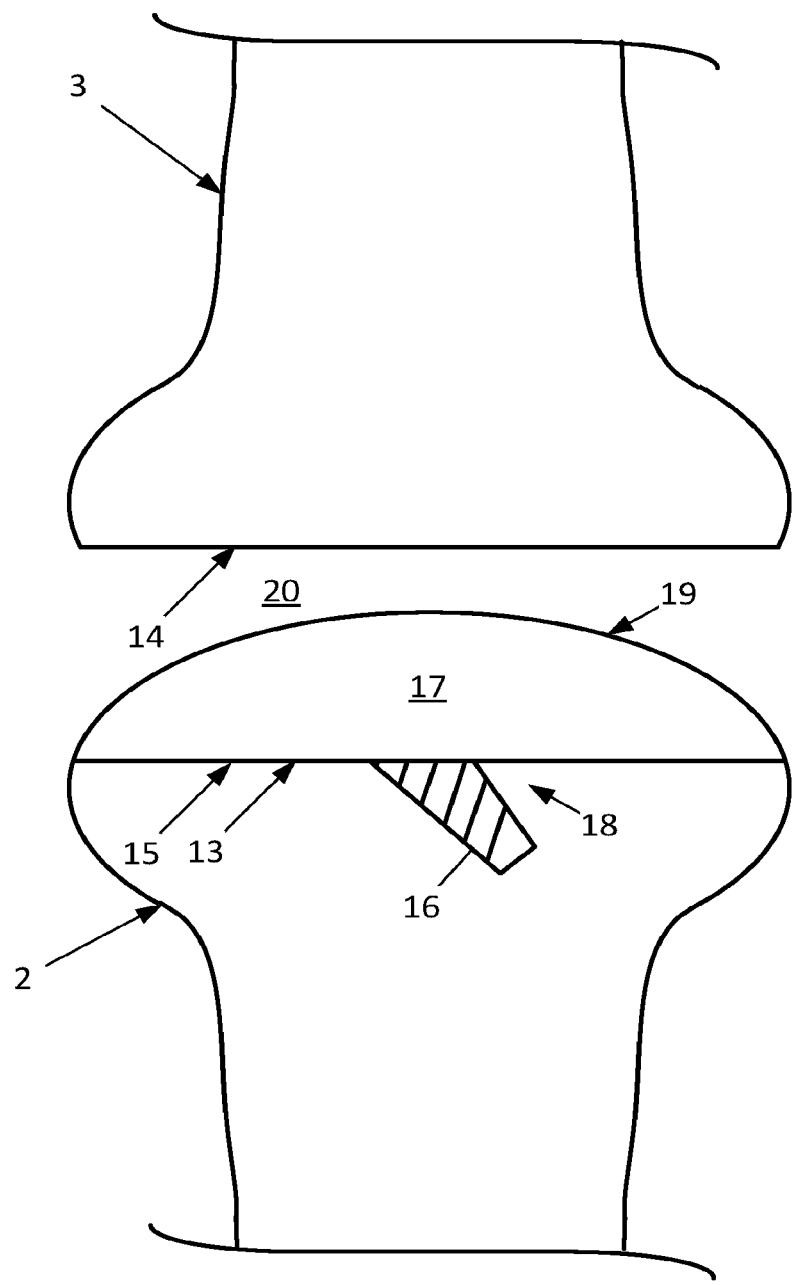
FIG. 8A illustrates a side view of a first implant system installed in the first bone.

Once the cooperating implant anchors 16 have been secured to the first bone 2, the cooperating implant 17, FIG. 8A, may be advanced into the removed space between the bones 2, 3 and secured to the cooperating implant anchor(s) 16 to form the cooperating implant system 18. As noted above, the cooperating implant 17 includes a cooperating implant load bearing surface 19 having a contour that is based on and/or substantially corresponds to the contours of the patient's removed articular surface 4. Optionally, the cooperating implant 17 may include an implant bone facing surface 15 having a contour that substantially corresponds to the contour of the first excision site 13 and/or is revolved around the longitudinal axis Lit of the cooperating implant anchor 16.

The cooperating implant anchor 16 and the cooperating implant 17 may include a first and a second fixation element, respectively, configured to secure, couple, mount, and/or fix the cooperating implant 17 to the cooperating implant anchor 16 such that the cooperating implant 17 is retained in the first excision site 13. According to one embodiment, the first and second fixation elements may be formed/defined by and/or extend from/to a proximal end of the cooperating implant anchor 16 and bone facing surface of the cooperating implant 17. The first and second fixation elements may be configured to form a friction connection (such as, but not limited to, a tapered connection including a Morse connection having tapered male and female friction surfaces), a positive mechanical engagement connection (e.g., but not limited to, a snap-fit connection or the like), and/or any other mechanism for connecting the cooperating implant 17 to the cooperating implant anchor 16.

Figure 8B:
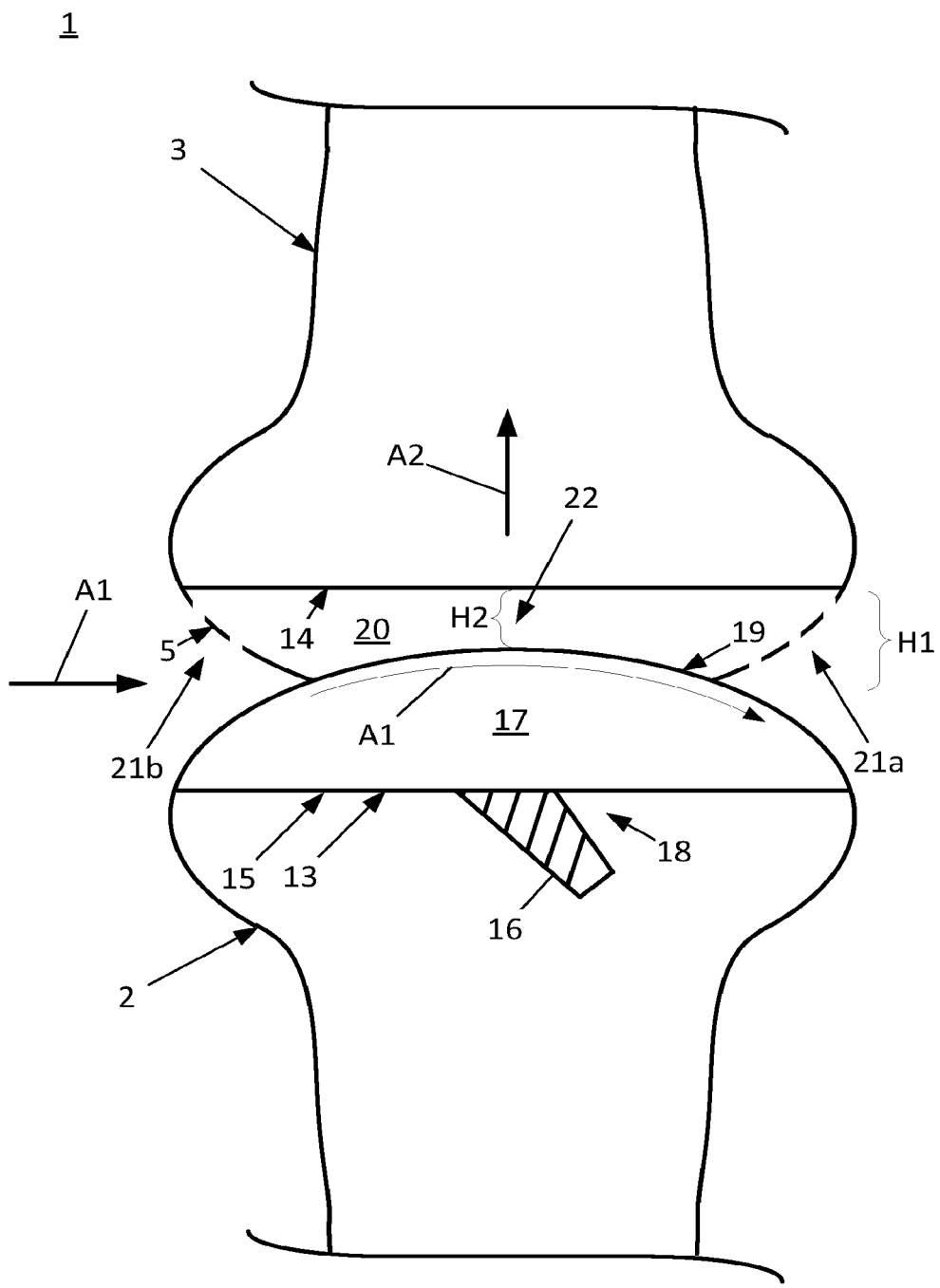
FIG. 8B illustrates a side view of a first implant system installed in the first bone and the removed articular surface of the second bone for illustrative purposes.

With reference to FIG. 8B, the cooperating implant system 18 is shown installed in the first excision site 13, and the removed second articular 5 is shown in dotted lines. As may be appreciated, the second implant system will include a load bearing surface having a contour that is based on and/or substantially corresponds to the contour of the removed second articular surface 5. Thus, the space defined between the second excision site 14 and the removed articular surface 5 may be thought as corresponding to the overall size and shape of the second implant of the second implant system, and the removed articular surface 5 shown in dotted lines can be thought as being the same as the load bearing surface of the second implant.

Because the second implant is to be advanced into the second excision site 14 in space 20 between the cooperating implant system 18 and the second excision site 14 (e.g., initially generally in the direction of arrow A1, which is generally perpendicular to the length of the first and second bones 2, 3), it may be difficult and/or impossible to fit a second implant system similar to the cooperating implant system 18 due to the overall necessary size, shape, and contour of the implant of the second implant system. In particular, the space 20 between the cooperating implant load bearing surface 19 and the second excision site 14 has a height H1 proximate a distal region 21a (e.g., a point generally furthest in the direction A that the second implant of the second implant system is to be inserted into the space 20) that is larger than the height H2 of an intermediate region 22 of the space 20 (e.g., a region between the distal region 21a and a proximal region 21b) where the second implant is to be located when installed in the second excision site 14. As used herein, the distal region 21a and proximal region 21b are defined by the direction that the drill bits move when the first and second excision sites 13, 14 are formed. While it may be possible to separate the first and second bones 2, 3, (e.g., move the first and second bones 2, 3 relative to each) to increase the space 20, separating the bones 2, 3 may be undesirable as it may damage connect tissue and/or cause additional discomfort to the patient.

The present disclosure addresses this problem by using a second implant system that includes a multicomponent implant system. As described herein, the multicomponent implant system includes one or more multicomponent implant anchors, one or more base plates configured to be secured to the multicomponent implant anchors, and one or more load plates configured to be slidably received and coupled to the base plate. The load plate includes the load bearing surface which has a contour based on and/or substantially corresponding to the contour of the removed second articular surface 5, and a load plate interface surface that has a contour substantially corresponding to the contour of the load bearing surface. The base plate has a bone facing surface which engages with multicomponent implant anchor within the second excision site 14, and a base plate interface surface. The base plate interface surface has a contour (at least in the distal 21a to proximal 21b direction) that also substantially corresponds to the contour of the load plate interface surface (at least in the distal 21a to proximal 21b direction).

The load plate interface surface is configured to be advanced into a space between the base plate interface surface and the cooperating implant system 18 generally along an arcuate direction having a curvature substantially corresponds to the contour of the load plate interface surface (at least in the distal 21a to proximal 21b direction). The load plate interface surface and the base plate interface surface may form a tongue and groove style connection wherein the tongue and groove may have any interlocking shape. As a result, the base plate may be installed in the second excision site 14 and the load plate may be slide into the space between the base plate and the cooperating implant system 18 without having to separate the first and second bones 2, 3.

Figure 9:
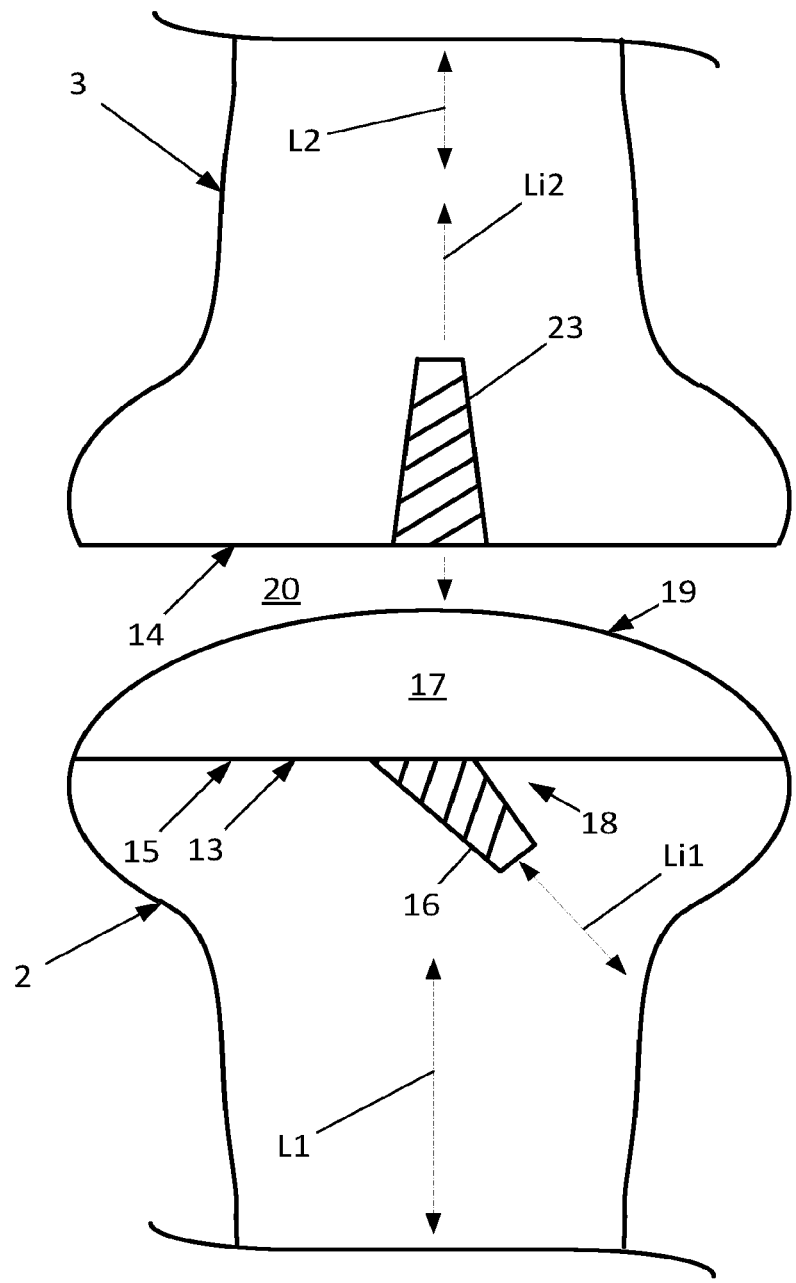
FIG. 9 illustrates a side view of an anchor installed in the second bone.

Turning now to FIG. 9, after the cooperating implant system 18 has been installed in the first excision site 12 of the first bone 2, one or more multicomponent implant anchors 23 of the multicomponent implant system are secured to the second bone 3 within the second implant site 14. The position of the multicomponent implant anchor(s) 23 with respect to the second excision site 14 may be determined using one or more guides or the like. The multicomponent implant anchor 23 may include one or more threaded portions, barbed portions, ribs, protrusions, or the like (which may, for example, extend circumferentially fully or partially around all or a portion of the shank of the anchor 23) configured to engage and retain the multicomponent implant anchor 23 to the second bone 3 within one or more of the overlapping generally cylindrical excision sections 12a, 12b (not visible in FIG. 9). The multicomponent implant anchor 23 may include a longitudinal axis Li2 that may be disposed generally parallel to the longitudinal axis L2 of the second bone 3; however, it should be understood that longitudinal axis Li2 may be disposed at any angle between 0 and 90 degrees (such as, but not limited to, between 30 and 80 degrees, between 40 and 60 degrees, or the like). It should also be understood that in embodiments where the multicomponent implant system includes multiple multicomponent implant anchors 23, the longitudinal axes Li2 two or more of the multicomponent implant anchors 23 may be disposed at the same and/or different angles with respect to the longitudinal axis L2 of the second bone 3.

Figure 10:
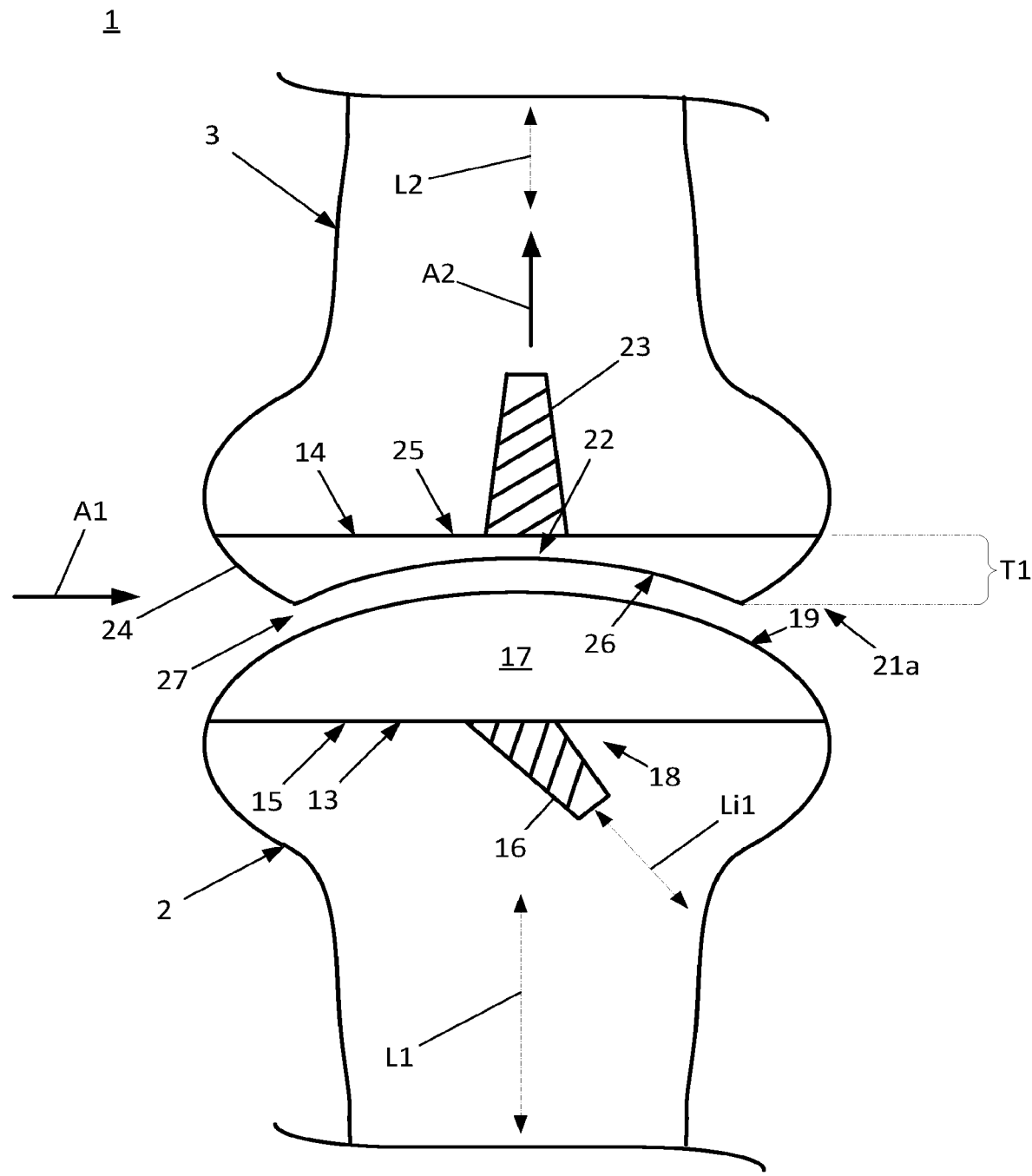
FIG. 10 illustrates a side view of a base plate coupled to the anchor in the second bone.

Next, at least one base plate 24 is advanced into the space 20 between the second excision site 14 and the load bearing surface 19 of the cooperating implant system 18, and the base plate 24 is secured to one or more of the multicomponent implant anchor(s) 23 as generally illustrated in FIG. 10. The multicomponent implant anchor 23 and the base plate 24 may include a first and a second fixation element, respectively, configured to secure, couple, mount, and/or fix the base plate 24 to the multicomponent implant anchor 23 such that the base plate 24 is retained in the second excision site 14. According to one embodiment, the first and second fixation elements may be formed/defined by and/or extend from/to a proximal end of the multicomponent implant anchor 23 and bone facing surface of the base plate 24. The first and second fixation elements may be configured to form a friction connection (such as, but not limited to, a tapered connection including a Morse connection having tapered male and female friction surfaces), a positive mechanical engagement connection (e.g., but not limited to, a snap-fit connection or the like), and/or any other mechanism for connecting the base plate 24 to the multicomponent implant anchor 23.

The base plate 24 includes a base plate bone facing surface 25 and a base plate interface surface 26. The base plate bone facing surface 25 may have a contour that substantially corresponds to the contour of the second excision site 14 and/or is revolved around the longitudinal axis Li2 of the multicomponent implant anchor 23. The base plate interface surface 26 has a contour and/or curvature that substantially corresponds to and/or is based on the contour and/or curvature of the patient's removed articular surface 5 (at least in the distal 21a to proximal 21b direction).

The base plate 24 may have a maximum thickness T1 in the distal region 21a that is less than the height H2 of an intermediate region 22 of the space 20. Because the maximum thickness T1 in the distal region 21a is less than the height H2 of an intermediate region 22 of the space 20, the base plate 24 may be advanced into the space 20 initially in the direction of arrow A1 and secured to the multicomponent implant anchor(s) 23 (e.g., by moving in the generally in the direction of arrow A2) within the second excision site 14 without having to separate the first and second bones 2, 3. Additionally, because the base plate interface surface 26 has a contour and/or curvature that substantially corresponds to and/or is based on the contour and/or curvature of the patient's removed articular surface 5 (at least in the distal 21a to proximal 21b direction), an implant space 27 is formed between the base plate interface surface 26 and the load bearing surface 19 of the cooperating implant system 18 having substantially coplanar curved surfaces.

Figure 11:
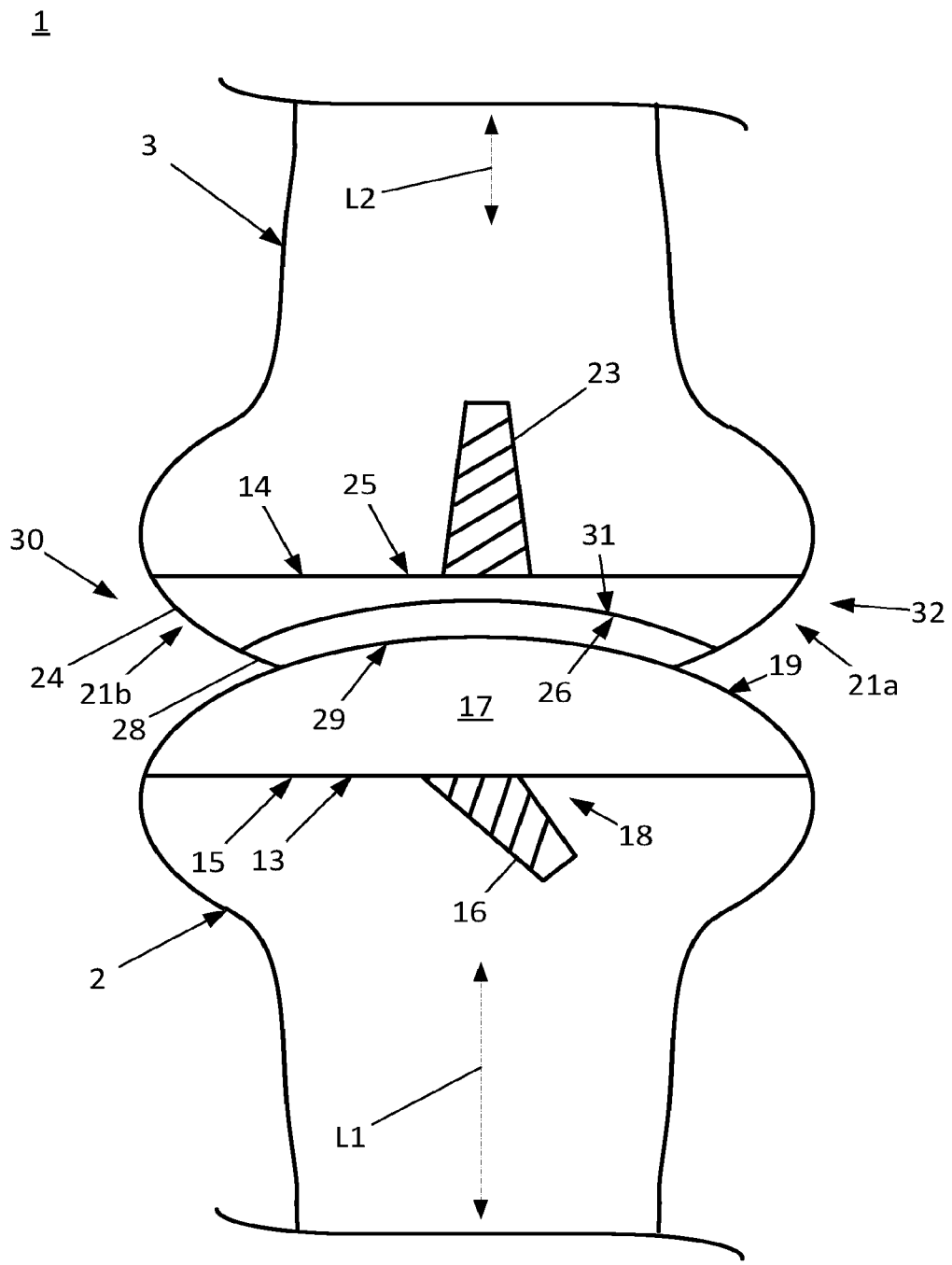
FIG. 11 illustrates a side view of a load plate coupled to the base plate to form a multicomponent implant system.
Figure 12:
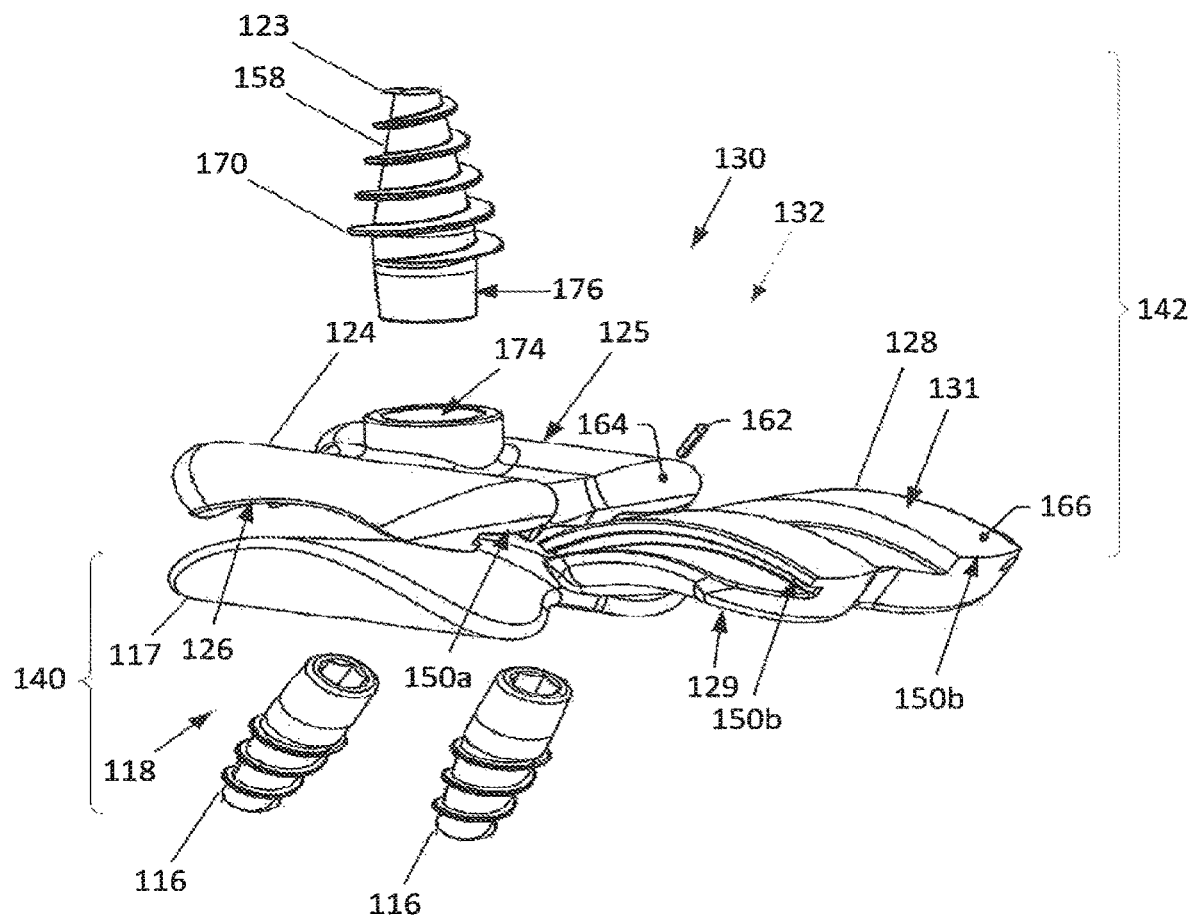
FIG. 12 is a side perspective view of the first and second implant systems in an exploded state.
Figure 13:
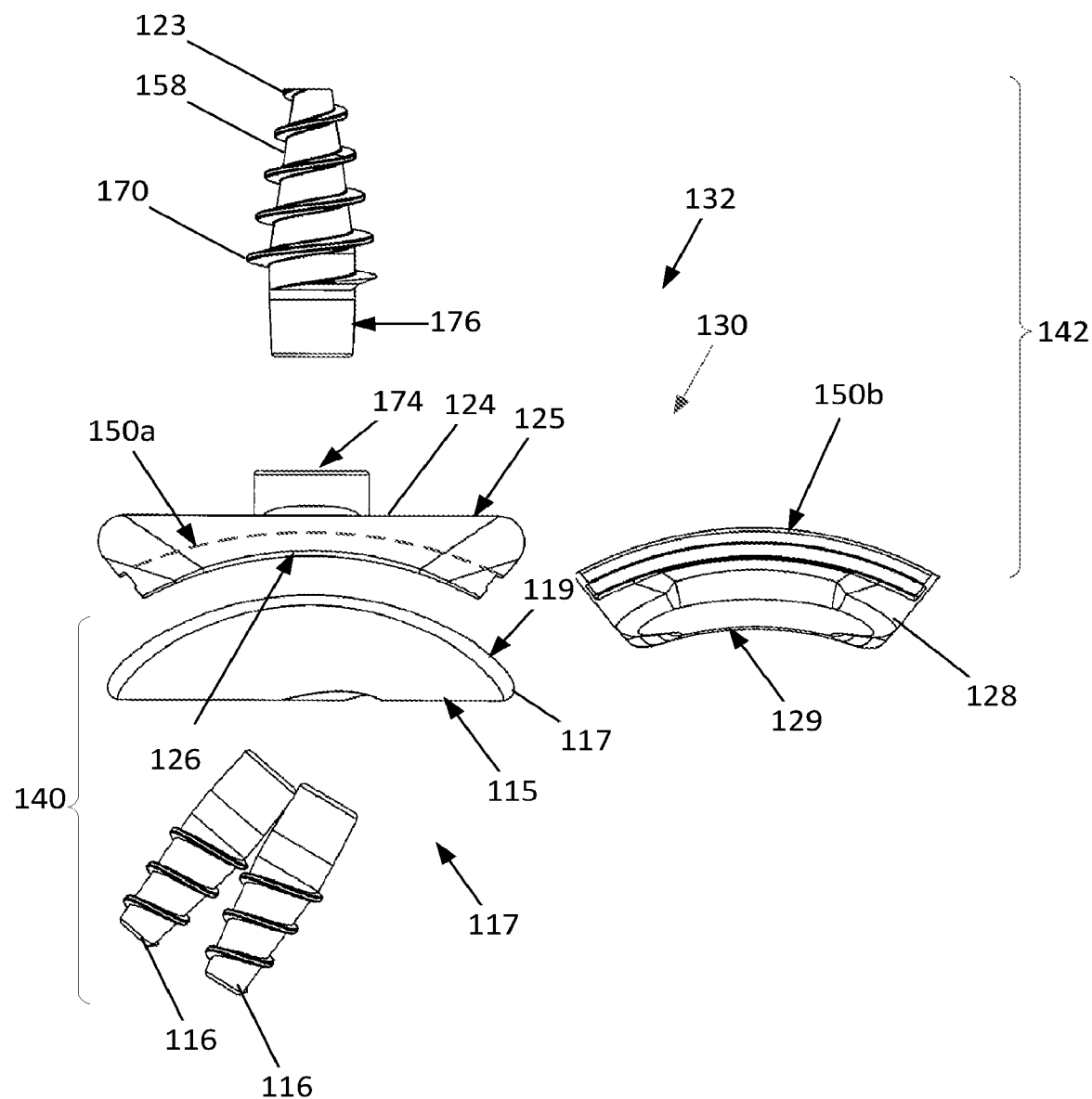
FIG. 13 is a side plan view of the first and second implant systems of FIG. 12.
Figure 14:
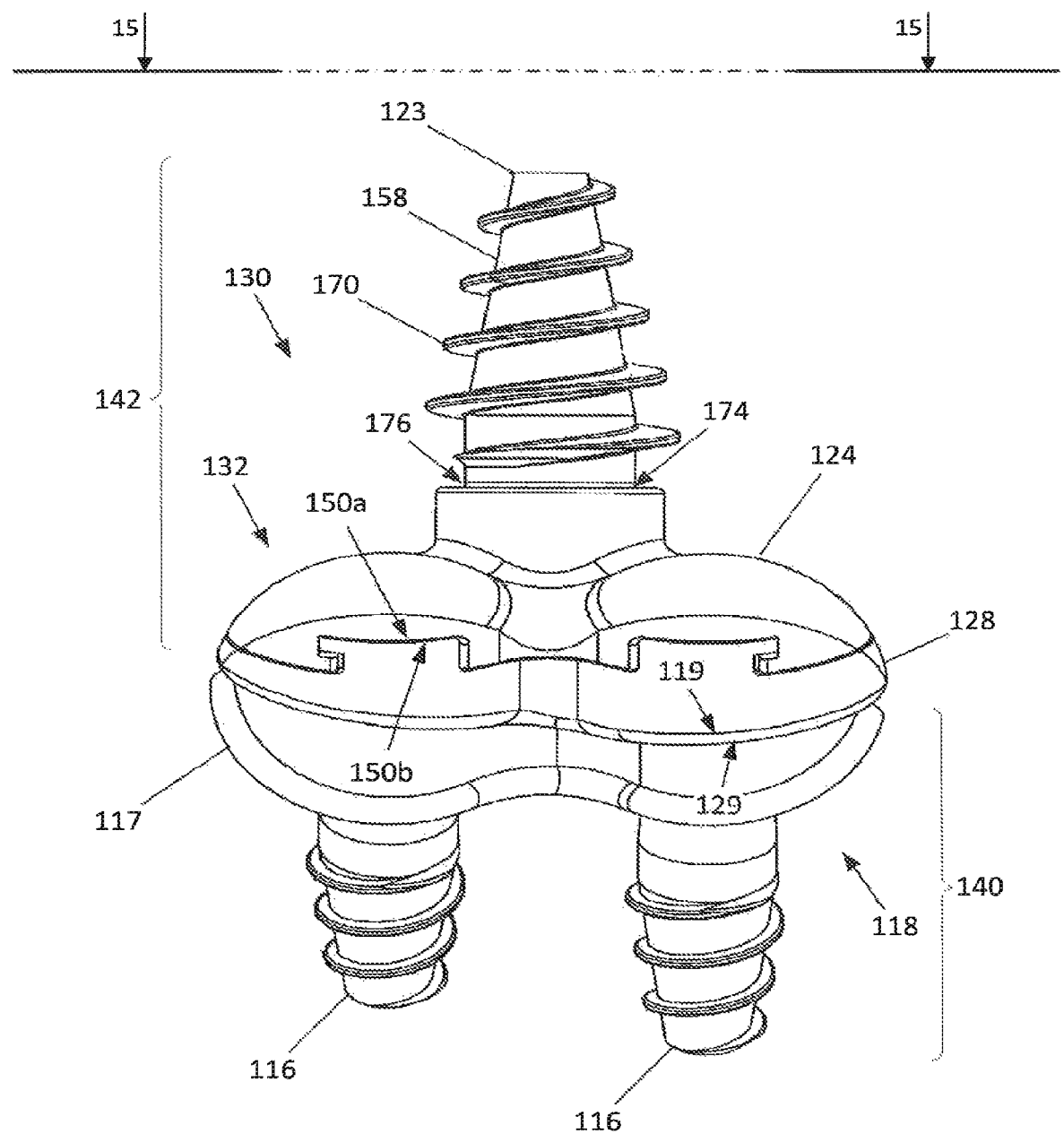
FIG. 14 is a front plan view of the first and second implant systems of FIG. 12 in an assembled state.
Figure 15:
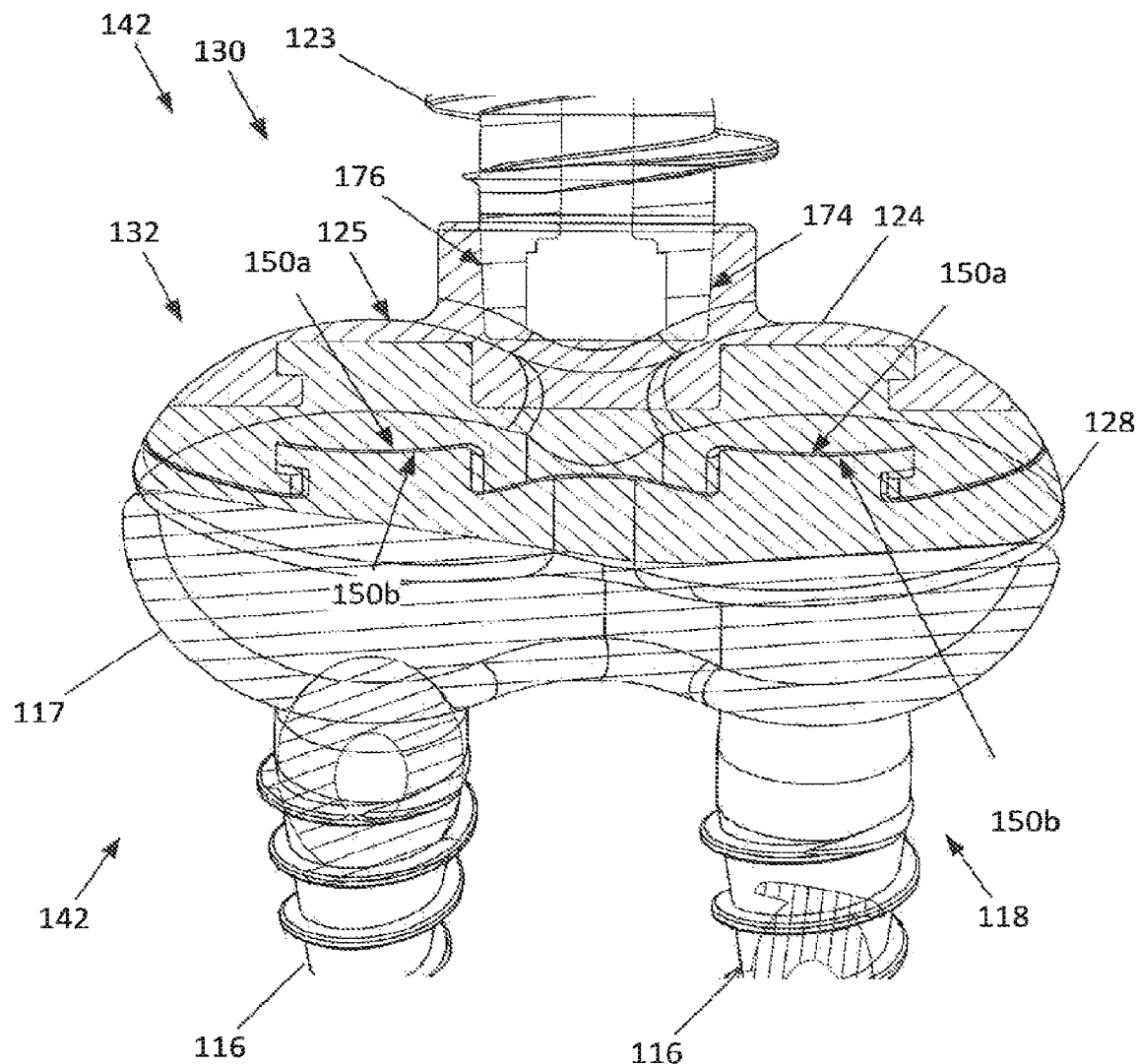
FIG. 15 is a front cross-sectional view of the first and second implant systems of FIG. 14 taken along lines 15-15.
Figure 16:
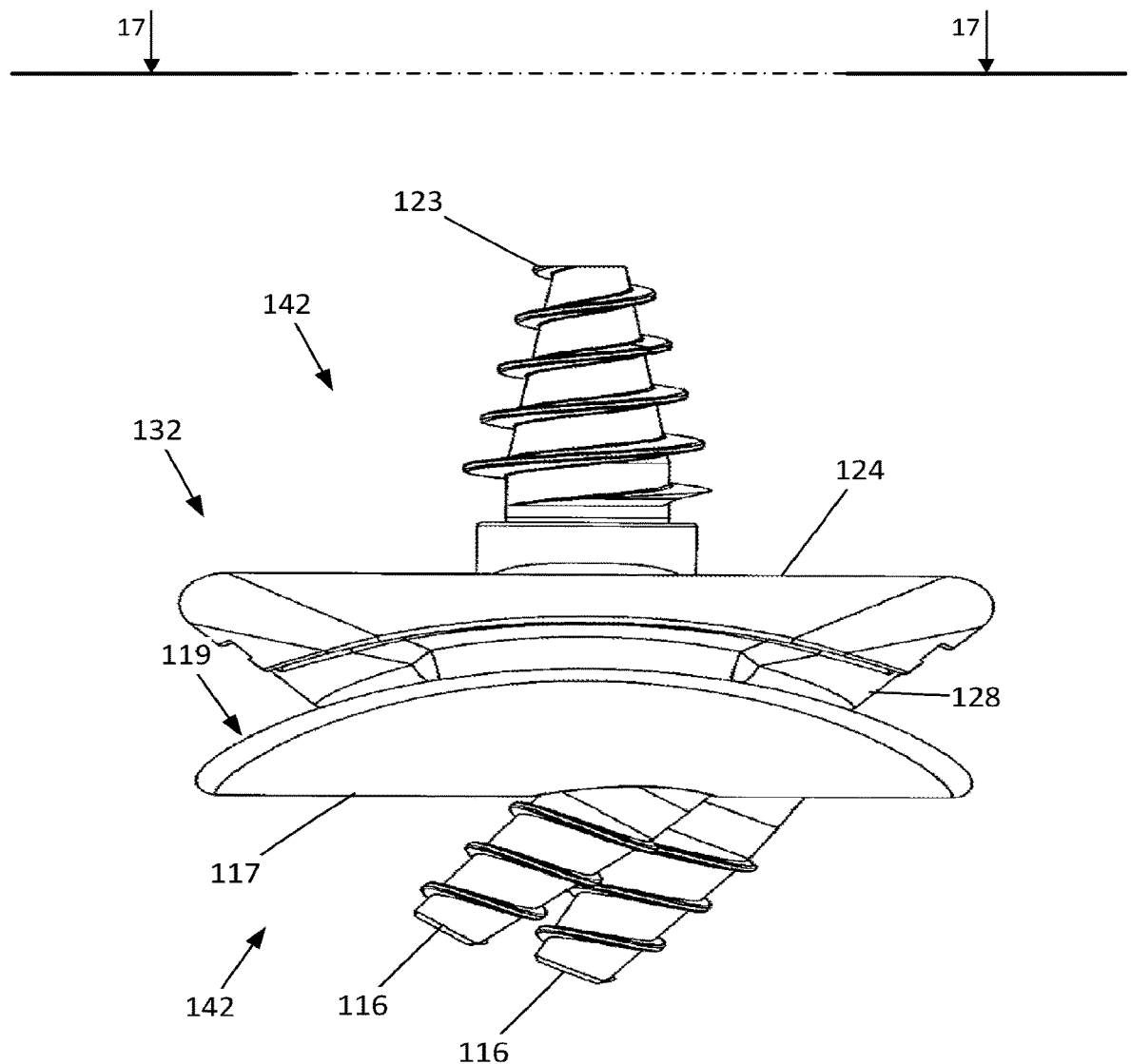
FIG. 16 is a side plan view of the first and second implant systems of FIG. 14.
Figure 17:
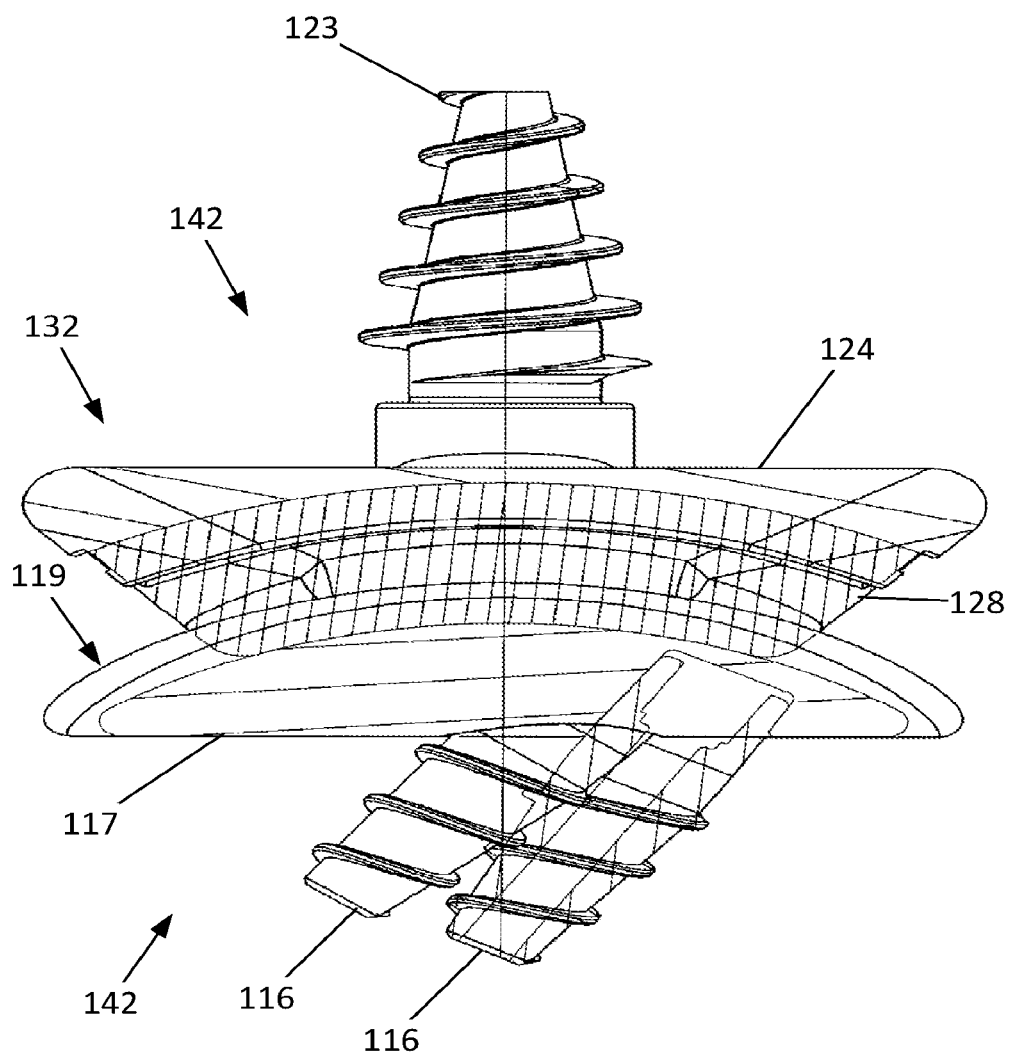
FIG. 17 is a side cross-sectional view of the first and second implant systems of FIG. 16 taken along lines 17-17.
Figure 18:
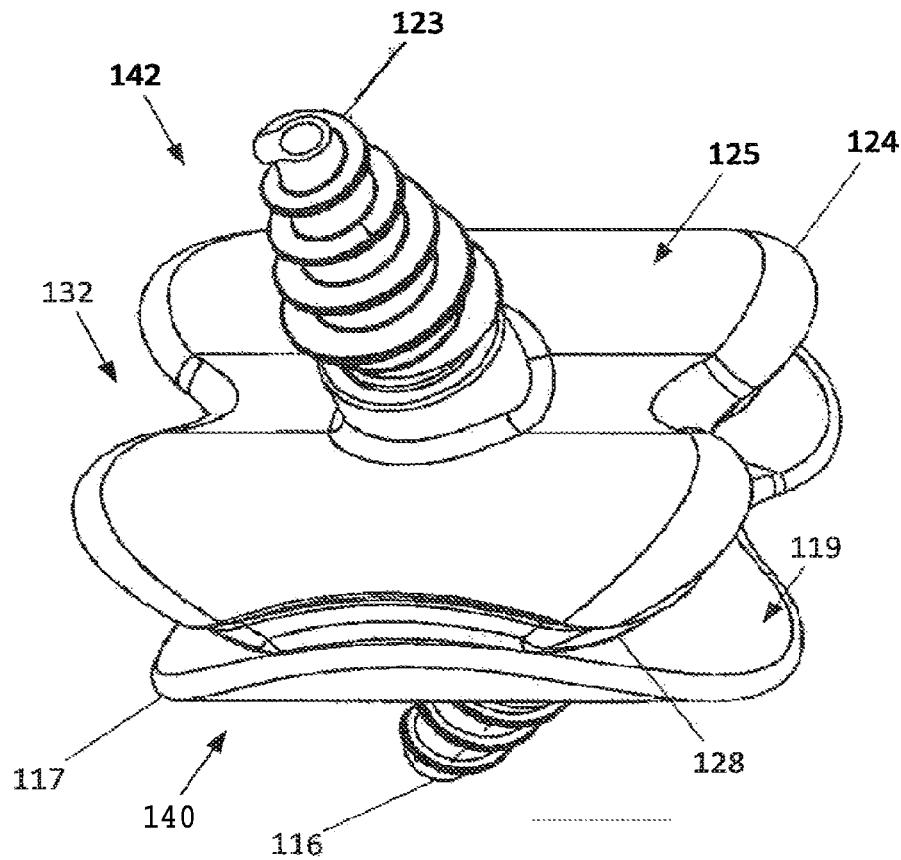
FIG. 18 is a top perspective view of the first and second implant systems of FIG. 14.
Figure 19:
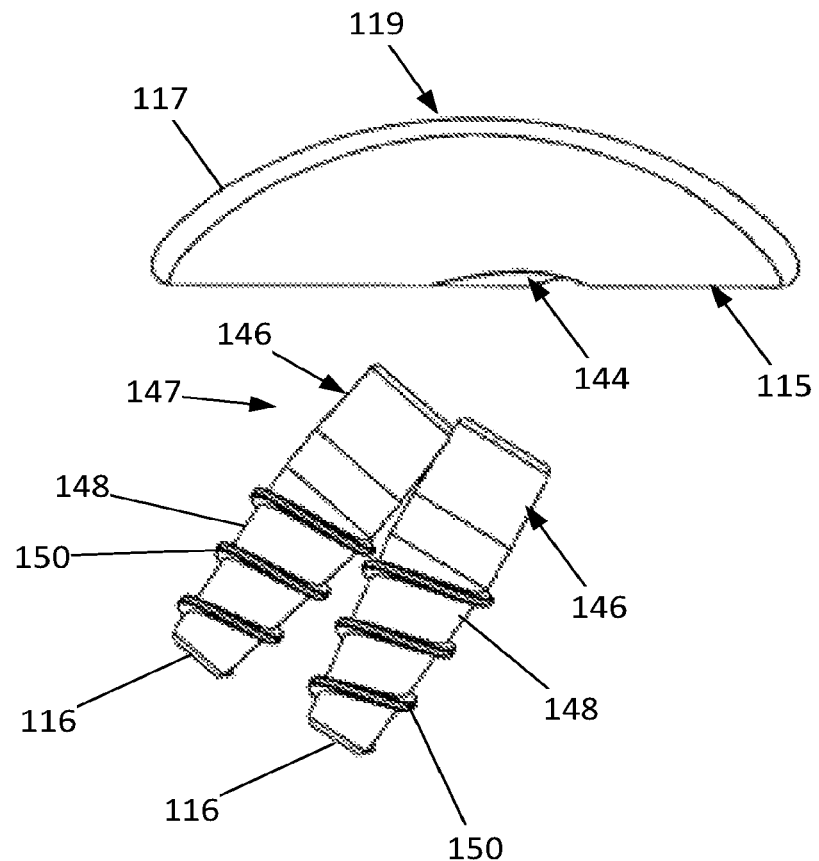
FIG. 19 is a side plan view of just the first implant system of FIG. 12.
Figure 20:
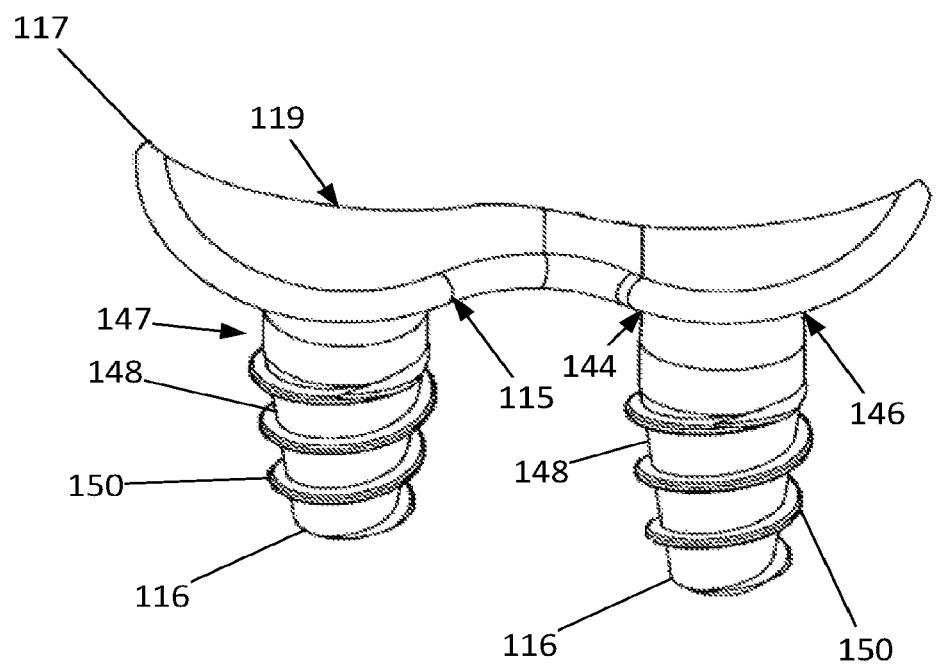
FIG. 20 is a front plan view of just the first implant system of FIG. 14.
Figure 21:
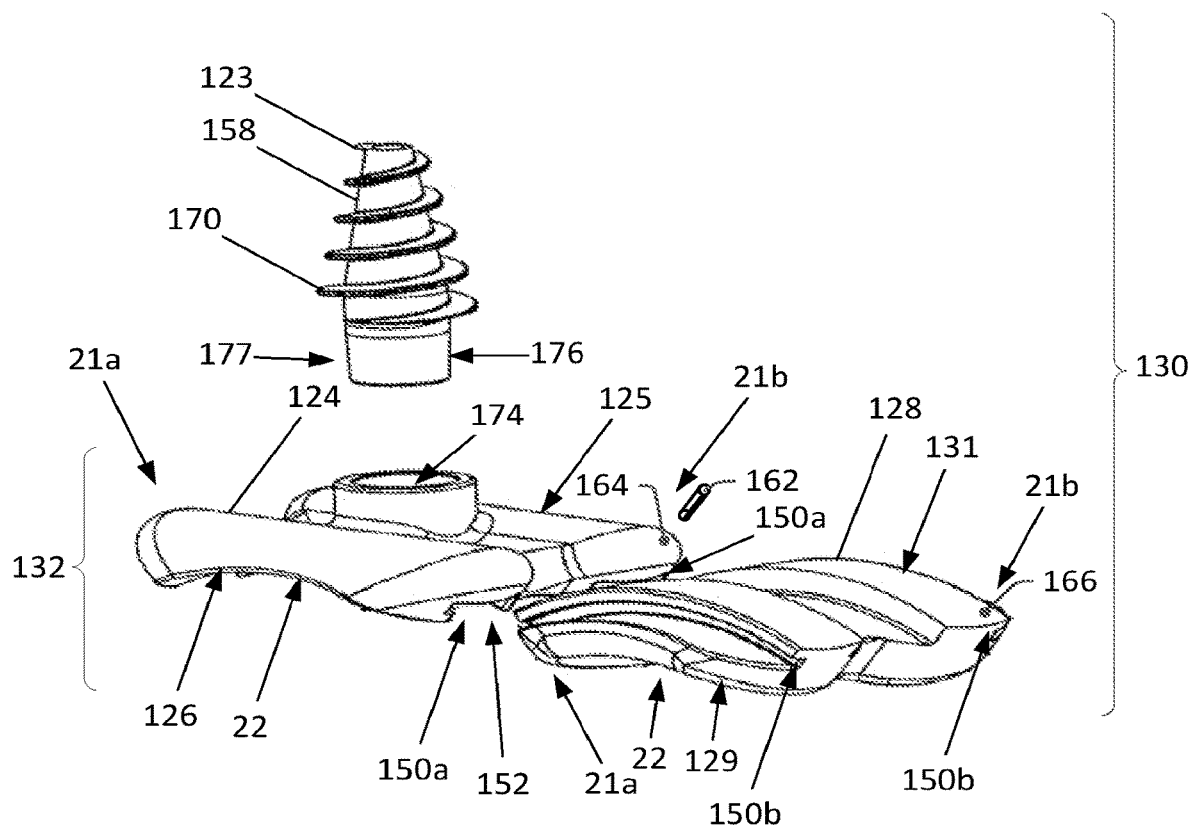
FIG. 21 is a perspective view of just the second implant system of FIG. 12.
Figure 22:
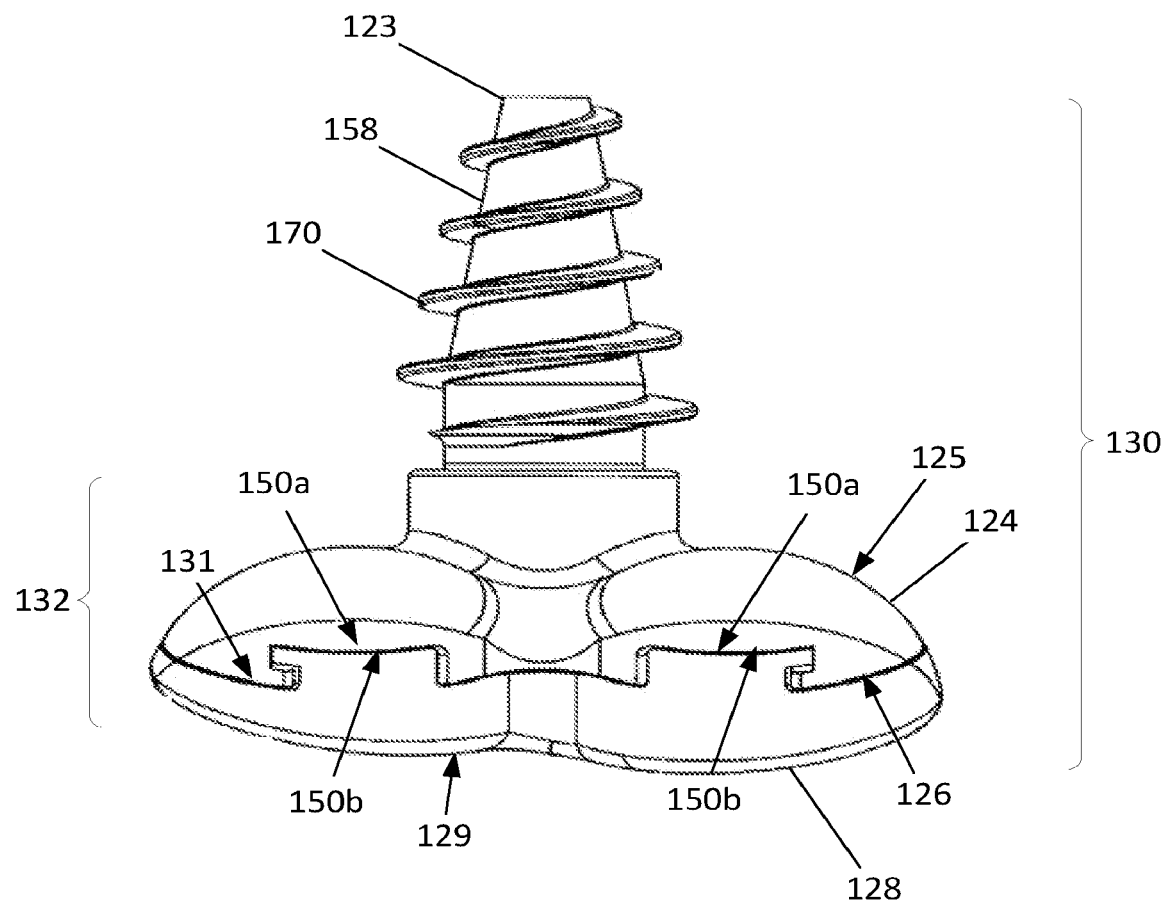
FIG. 22 is a front view of just the second implant system of FIG. 14.

Once the base plate 24 is secured to the multicomponent implant anchor 23 within the second excision site 14, the load plate 28 is advanced into the implant space 27 and secured to the base plate 24 to form the multicomponent implant 32 of the assembled multicomponent implant system 30, e.g., as generally illustrated in FIG. 11. The load plate 28 includes a load bearing surface 29 and a load plate interface surface 31. As noted herein, the load bearing surface 29 has a contour that is based on and/or substantially corresponds to the contours of the patient's removed articular surface 5.

As noted herein, the load plate interface surface 31 includes a tongue and groove style connection with the base plate interface surface 26 of the base plate 24 such that the load plate 28 may be advanced/slid relative to the base plate 24 and form a connection therebetween. The load plate interface surface 31 has a contour and/or curvature that substantially corresponds to and/or is based on the contour and/or curvature of the patient's removed articular surface 5 and/or load bearing surface 29 (at least in the distal 21a to proximal 21b direction). In addition, the load plate interface surface 31 has a contour and/or curvature (at least in the (at least in the distal 21a to proximal 21b direction) that substantially corresponds to and/or is based on the contour and/or curvature of the base plate interface surface 26. As such, the load bearing surface 29 and the load plate interface surface 31 of the load plate 28 as well as the base plate interface surface 26 of the base plate 24 are substantially coplanar curved surfaces, and the load plate 28 may be advanced into the implant space 27 and secured to the base plate 24 (e.g., by advancing the tongue and groove connection between the base plate interface surface 26 and the load plate interface surface 31), without having to separate the first and second bones 2, 3 even after the cooperating implant system 18 has been installed in the first excision site 13.

Turning now to FIGS. 12-18, one embodiment of a first implant system 140 and a second implant system 142 which may be used with the systems and methods described herein are generally illustrated. In the illustrated embodiment, the first implant system 140 includes a cooperating implant system 118 and the second implant system 142 includes a multicomponent implant system 130. It should be appreciated, however, that the first implant system 140 may include any implant system described herein and/or known to those skilled in the art. For example, both the first and second implant systems 140, 142 may be a multicomponent implant system 130.

Turning now to FIGS. 12-18, one embodiment of a first implant system 140 and a second implant system 142 which may be used with the systems and methods described herein are generally illustrated. In particular, FIGS. 12-13 generally illustrate one embodiment of the first and second implant system 140, 142 in an exploded state. While the first implant system 140 will be described in terms of a cooperating implant system 118 and the second implant system 142 will be described includes a multicomponent implant system 130, it should be appreciated that the first implant system 140 may include any implant system described herein and/or known to those skilled in the art. For example, both the first and second implant systems 140, 142 may be a multicomponent implant system 130. With reference to FIGS. 14-18, it can be seen that the first and second implant systems 140, 142 include implant portions 117, 132 having a cross-sectional shape generally corresponding to the two or more overlapping generally cylindrical excision sections 12a, 12b formed in the first and second bones 2, 3 by the generally cylindrical pathways of two or more adjacent overlapping drilling bits as generally illustrated in FIG. 5.

With reference to FIGS. 12-18 and 19-20, the cooperating implant system 118 includes a cooperating implant 117 configured to be coupled, mounted, and/or otherwise secured to one or more cooperating implant anchors 116. The cooperating implant 117 includes an implant bone facing surface 115 and a load bearing surface 119 (see, e.g., FIG. 13). As can be seen, the implant bone facing surface 115 has a contour that at least partially corresponds to the truncated generally cylindrical cross-sectional contour of the first excision site 13, while the load bearing surface 119 may have a contour that is based on and/or substantially corresponds to the contours of the patient's removed articular surface 4. As such, the cooperating implant 117 may be considered to have a truncated generally cylindrical cross-sectional shape corresponding to the remove portion of the patient's first bone 2 defined by the intersection of the generally cylindrical pathways of the two adjacent partially overlapping drilling bits and the first bone 2.

The implant bone facing surface 115 may include one or more fixation elements 144 (see, e.g., FIG. 19) configured to engage with one or more corresponding fixation elements 146 of the cooperating implant anchors 116 to secure, couple, mount, and/or fix the cooperating implant 117 to the cooperating implant anchor 116 such that the cooperating implant 117 is retained in the first excision site 13. According to one embodiment, the first and second fixation elements 144, 146 may be configured to form a friction connection (such as, but not limited to, a tapered connection including a Morse connection having tapered male and female friction surfaces), a positive mechanical engagement connection (e.g., but not limited to, a snap-fit connection or the like), and/or any other mechanism for connecting the cooperating implant 117 to the cooperating implant anchor 116. In the illustrated embodiment, the implant bone facing surface 115 defines a tapered female recess while the distal end region 147 of the shank 148 defines a tapered, male protrusion; however, it should be appreciated that this arrangement may be reversed.

At least a portion the shank 148 of the cooperating implant anchor 116 may include one or more threaded portions, barbed portions, ribs, protrusions, or the like 150 (which may, for example, extend circumferentially fully or partially around all or a portion of the shank 148 of the anchor 116) configured to engage and retain the cooperating implant anchor 116 to the first bone 2 within one or more of the overlapping generally cylindrical excision sections 12*a*, 12*b*. The shank 148 may optionally be cannulated, and may be configured to be advanced over a guide pin (not shown). The guide pin may be located in the generally cylindrical excision sections 12*a*, 12*b* using a guide (not shown).

Turning now to FIGS. 12-18 and 21-22, the multicomponent implant system 130 includes a multicomponent implant 132 configured to be coupled, mounted, and/or otherwise secured to one or more multicomponent implant anchors 123. The multicomponent implant 132 includes base plate 124 and a load plate 128. The base plate 124 includes a base plate bone facing surface 125 and the load plate 128 includes a load bearing surface 129. As can be seen, the base plate bone facing surface 125 has a contour that at least partially corresponds to the truncated generally cylindrical cross-sectional contour of the second excision site 14, while the load bearing surface 129 may have a contour that is based on and/or substantially corresponds to the contours of the patient's removed articular surface 5. As such, the multicomponent implant 132 may be considered to have a truncated generally cylindrical cross-sectional shape corresponding to the remove portion of the patient's second bone 3 defined by the intersection of the generally cylindrical pathways of the two adjacent partially overlapping drilling bits and the second bone 3.

The multicomponent implant bone facing surface 125 may include one or more fixation elements 174 configured to engage with one or more corresponding fixation elements 176 of the multicomponent implant anchor 123 to secure, couple, mount, and/or fix the base plate 124 to the multicomponent implant anchor 123 such that the base plate 124 is retained in the second excision site 14. According to one embodiment, the first and second fixation elements 174, 176 may be configured to form a friction connection (such as, but not limited to, a tapered connection including a Morse connection having tapered male and female friction surfaces), a positive mechanical engagement connection (e.g., but not limited to, a snap-fit connection or the like), and/or any other mechanism for connecting the base plate 124 to the multicomponent implant anchor 123. In the illustrated embodiment, the multicomponent implant facing surface 125 defines a tapered female recess while the distal end region 177 of the shank 158 defines a tapered, male protrusion; however, it should be appreciated that this arrangement may be reversed.

At least a portion the shank 158 of the multicomponent implant anchor 123 may include one or more threaded portions, barbed portions, ribs, protrusions, or the like 170 (which may, for example, extend circumferentially fully or partially around all or a portion of the shank 158 of the anchor 123) configured to engage and retain the multicomponent implant anchor 123 to the second bone 3 within one or more of the overlapping generally cylindrical excision sections 12*a*, 12*b*. The shank 158 may optionally be cannulated, and may be configured to be advanced over a guide pin (not shown). The guide pin may be located in the generally cylindrical excision sections 12*a*, 12*b* using a guide (not shown).

The base plate 124 and the load plate 128 each include one or more base plate interface surfaces 126 and load plate interface surfaces 131, respectively. The base plate interface surfaces 126 and load plate interface surfaces 131 may form a tongue and groove style connection 150*a*, 150*b* such that the load plate 128 may be slid into engagement with the base plate 124 along a generally arcuate direction (e.g., arcuate direction A1 extending generally from the proximal region 21*b* to the distal region 21*a* as generally illustrated in FIG. 8B).

In the illustrated embodiment, the base plate interface surfaces 126 includes one or more grooves 150*a* and the load plate interface surfaces 131 includes one or more tongues 150*b* (though it should be appreciated that the arrangement of one or more tongues and grooves may be reversed). The groove 150*a* may extend from an opening 152 in the proximal region 21*b* (e.g., front) of the base plate 124 towards the distal region 21*a* (e.g., back) of the base plate 124. For example, the groove 150*a* may extend all the way to an opposite opening in the distal region 21*a* of the base plate 124. Alternatively (or in addition), the groove 150*a* may extend partially to the distal region 21*a* such that groove 150*a* includes an end region that is separate from and does not reach the distal most portion of the distal region 21*a*. In this embodiment, the end region of the groove 150*a* may function as a locator that prevents the load plate 128 from being advanced too far with respect to the base plate 124, and thereby align the base plate 124 and the load plate 128 when assembling the multicomponent implant 132. Similarly, the tongue 150*b* may extend from the distal region (e.g., back) 21*a* of the load plate 128 towards the proximal region 21*b* (e.g., front) of the load plate 128. For example, the tongue 150*b* may extend all the way to the proximal region 21*b* of the load plate 128. Alternatively (or in addition), the tongue 150*b* may extend partially to an end region of the load plate 128 such that tongue 150*b* does not reach the proximal most portion of the proximal region 21*b*. In this embodiment, the end region of the tongue 150*b* may function as a locator that prevents the load plate 128 from being advanced too far with respect to the base plate 124, and thereby align the base plate 124 and the load plate 128 when assembling the multicomponent implant 132.

The tongue and groove style connection 150a, 150b may be configured to allow the base plate 124 to be installed in the second excision site 14 and the load plate 128 to be slid along the generally arcuate direction A1 from the proximal region 21b of the base plate 124 in the space between the base plate 124 and the cooperating implant system 118 without having to separate the first and second bones 2, 3. The tongue and groove connection 150a, 150b may include a tongue and groove having any interlocking shape such as, but not limited to, a T-shape, L-shape, Y-shape, dovetail shape, or the like.

In some embodiments, the load plate 128 may be mechanically secured to the base plate 124 with a mechanical lock to prevent the interfaces 126, 131 from sliding apart. Alternatively (or in addition), the tongue and groove connection 150a, 150b may form a friction fit connection, for example, where the tongue 150b partially deform the groove 150a the further the tongue 150b is slid into the groove 150a (or vice versa). The tongue 150b and/or groove 150a may exhibit a slight taper to create the friction fit. A set screw 162 may alternatively, or additionally to any of the embodiments above, be utilized to lock the load plate 128 relative the base plate 124. For example, a set screw 162 may be inserted into an opening 164 in the base plate 124 and may act against (e.g., engage) the load plate 128 by butting against the load plate 128 or is received in a blind hole 166 formed in the load plate 128, such that the screw 162 is trapped between the load plate 128 and the base plate 124.

In the embodiment shown, the base plate interface surface 126 and the load plate interface surface 131 include a first and a second tongue and groove 150a, 150b, each corresponding to one of the overlapping generally cylindrical excision sections 12a, 12b, respectively. It should be appreciated, however, that this is not a limitation of the present disclosure unless specifically claimed as such and that the number and placement of the tongues and grooves 150a, 150b may be located anywhere on the base plate interface surface 126 and the load plate interface surface 131.

The base plate interface surface 126 and the load plate interface surface 131 and/or the tongue and groove connections 150a, 150b may have contours and/or curvatures that substantially correspond to and/or are based on the contours and/or curvatures of the patient's removed articular surface 5 (at least in the distal 21a to proximal 21b direction). As such, the base plate interface surface 126 and the load plate interface surface 131 and/or the tongue and groove connections 150a, 150b may define surfaces that are arcuate and substantially coplanar.

Additionally, the base plate 124 may have a maximum thickness T1 in the distal region 21a that is less than the height H2 of an intermediate region 22 of the space 20 (see, e.g., FIGS. 8B and 10). Because the maximum thickness T1 in the distal region 21a is less than the height H2 of an intermediate region 22 of the space 20, the base plate 124 may be advanced into the space 20 initially in the direction of arrow A1 and secured to the multicomponent implant anchor(s) 123 (e.g., by moving in the generally in the direction of arrow A2) within the second excision site 14 without having to separate the first and second bones 2, 3. According to one embodiment, the maximum thickness T1 of the base plate 124 in the distal region 21a is less than 90% of the height H2 of an intermediate region 22 of the space 20, for example, less than 80% of the height H2, less than 70% of the height H2, less than 60% of the height H2, and/or less than 50% of the height H2, including any value and/or range therein.

A friction fit may be understood herein as a connection that relies upon friction to inhibit separation of the parts, particularly one where one part is compressed (deformed) against the other. Alternatively, or additionally, a positive mechanical engagement may be utilized, which is understood as a connection formed between the components that relies upon mechanical engagement and interlocking of the parts to inhibit separation (such as the use of overlapping surfaces, cotter pins passing through the connector and anchor base, set screws, etc.).

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. An implant system comprising:
   a multicomponent implant system comprising:
   a multicomponent implant having a proximal end and a distal end and a first axis extending therebetween when assembled, said multicomponent implant comprising:
   a load plate comprising a load bearing surface and a load plate interface surface, wherein said load bearing surface has a contour substantially corresponding to a contour of a removed portion of a patient's articular surface of a first bone of a patient's joint, and wherein said load plate interface surface has a contour along said first axis that substantially corresponds to the contour of the load bearing surface along said first axis; and
   a base plate comprising a bone facing surface comprising a first fixation element and an opposite base plate interface surface, said bone facing surface configured to engage said first bone within a first excision site beneath said removed portion of said patient's articular surface, and said base plate interface surface having a contour along said first axis that substantially corresponds to the contour of the load plate interface surface along said first axis; and
   a multicomponent implant anchor configured to be detachably coupled to the base plate, the multicomponent implant anchor comprising a second fixation element configured to couple with said first fixation element, wherein said multicomponent implant anchor is configured to be secured to said first bone and to secure said base plate within said first excision site;
   wherein said multicomponent implant is configured to interface with a cooperating implant system configured to replace at least a portion of an articular surface associated with a removed portion of a second bone of said patient's joint, wherein said second bone is located at a position adjacent to said first bone, wherein said multicomponent implant is configured to be received between said first excision site and said cooperating implant system, and wherein said load plate is configured to be advanced in an arcuate direction to slidably couple said load plate to said base plate after said base plate has been secured within said first excision site.

2. The implant system of claim 1, wherein said bone facing surface and said base plate interface surface are substantially parallel.

3. The implant system of claim 1, wherein said base plate interface surface has a curvature substantially corresponding to a curvature of said removed portion of said patient's articular surface along said first axis.

4. The implant system of claim 1, wherein said load plate interface surface and said base plate interface surface comprise a tongue and a groove configured to form a tongue and groove connection therebetween.

5. The implant system of claim 4, wherein at least one of said tongue and said groove extends partially between said proximal end and said distal end.

6. The implant system of claim 4, wherein said groove comprises an opening disposed on said proximal end of at least one of said load plate and said base plate.

7. The implant system of claim 4, wherein said tongue and said groove are configured to locate said load plate relative to said base plate.

8. The implant system of claim 7, wherein said tongue and said groove are configured to establish a maximum position of said load plate relative to said base plate along said arcuate direction.

9. The implant system of claim 1, wherein said base plate and said load plate, when coupled together, have a truncated generally cylindrical shape.

10. The implant system of claim 1, wherein said multicomponent implant is configured to be received in a space between said first excision site and an articulating surface associated with said second bone without separating said first bone relative to said second bone.

11. The implant system of claim 10, wherein a maximum height between said bone facing surface and said base plate interface surface of a distal end of said base plate is less than a minimum separation distance between said first bone within said first excision site and said articulating surface associated with said second bone associated with an intermediate region.

12. The implant system of claim 1, wherein said multicomponent implant, when assembled, has a shape generally corresponding to two or more partially overlapping truncated generally cylinders, wherein a length of said two or more partially overlapping truncated generally cylinders extends between said proximal end and said distal end.

13. The implant system of claim 1, further comprising said cooperating implant system.

14. The implant system of claim 13, wherein said multicomponent implant is configured to be received in a space between said first excision site and a load bearing surface of said cooperating implant system after said cooperating implant system is secured to said second bone and without separating said first bone relative to said second bone.

15. The implant system of claim 1, wherein the first and second fixation elements are configured to form a friction connection.

16. The implant system of claim 15, wherein the friction connection comprises a Morse connection comprising a tapered male and a tapered female friction surfaces.

17. The implant system of claim 1, wherein the first and second fixation elements are configured to form a positive mechanical engagement connection.

* * * * *